(12) United States Patent
Weber et al.

(10) Patent No.: US 8,795,348 B2
(45) Date of Patent: Aug. 5, 2014

(54) MEDICAL DEVICES AND RELATED METHODS

(75) Inventors: Jan Weber, Maple Grove, MN (US); Thomas J. Holman, Princeton, MN (US); Scott Schewe, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1954 days.

(21) Appl. No.: 11/152,555

(22) Filed: Jun. 14, 2005

(65) Prior Publication Data

US 2006/0282156 A1 Dec. 14, 2006

(51) Int. Cl.
*A61F 2/06* (2013.01)
*A61M 29/00* (2006.01)

(52) U.S. Cl.
USPC ........ 623/1.12; 623/1.11; 623/1.23; 606/191; 606/198

(58) Field of Classification Search
USPC ........ 606/191, 193, 195, 198; 623/1.11, 1.23, 623/1.12; 604/104–109; 607/116, 125, 126, 607/122, 98, 99
See application file for complete search history.

(56) References Cited

U.S. PATENT DOCUMENTS

| | | | |
|---|---|---|---|
| 4,753,223 A | 6/1988 | Bremer | |
| 5,238,005 A | 8/1993 | Imran | |
| 5,265,622 A | 11/1993 | Barbere | |
| 5,389,072 A | 2/1995 | Imran | |
| 5,782,899 A | 7/1998 | Imran | |
| 5,861,035 A * | 1/1999 | Griffith | 623/23.68 |
| 5,873,907 A | 2/1999 | Frantzen | |
| 5,997,526 A | 12/1999 | Giba et al. | |
| 6,071,305 A * | 6/2000 | Brown et al. | 623/1.43 |
| 6,261,316 B1 | 7/2001 | Shaolian et al. | |
| 6,312,407 B1 * | 11/2001 | Zadno-Azizi et al. | 604/103.03 |
| 6,375,638 B2 | 4/2002 | Nason et al. | |
| 7,258,696 B2 * | 8/2007 | Rabkin et al. | 623/1.11 |
| 2002/0188341 A1 | 12/2002 | Elliott | |
| 2003/0050684 A1 | 3/2003 | Abrams et al. | |
| 2005/0102017 A1 | 5/2005 | Mattison | |
| 2005/0131523 A1 | 6/2005 | Bashiri et al. | |
| 2005/0187602 A1 | 8/2005 | Eidenschnick | |
| 2005/0187603 A1 | 8/2005 | Eidenschnick et al. | |
| 2007/0016165 A1 * | 1/2007 | Von Oepen et al. | 604/525 |

FOREIGN PATENT DOCUMENTS

WO WO 02/087449 11/2002

OTHER PUBLICATIONS

U.S. Appl. No. 10/785,449, filed Feb. 24, 2004, and entitled "Rotatable Catheter Assembly".
U.S. Appl. No. 10/863,724, filed Jun. 8, 2004, and entitled "Bifurcated Stent Delivery System".
U.S. Appl. No. 10/915,209, filed Aug. 10, 2004, and entitled "Rotatable Catheter Assembly".
U.S. Appl. No. 11/111,511, filed Apr. 21, 2005, and entitled "Particles".
Schetsky, L. McDonald, "Shape Memory Alloys", Encyclopedia of Chemical Technology (3rd ed.), John Wiley & Sons, 1982, vol. 20. pp. 726-736.

* cited by examiner

*Primary Examiner* — Katherine Dowe
*Assistant Examiner* — Michael Mendoza
(74) *Attorney, Agent, or Firm* — Seager, Tufte & Wickhem LLC

(57) ABSTRACT

A medical system including an elongate member and an elongate element associated with the elongate member so that a shape of the elongate member can be altered upon applying energy to the element.

20 Claims, 19 Drawing Sheets

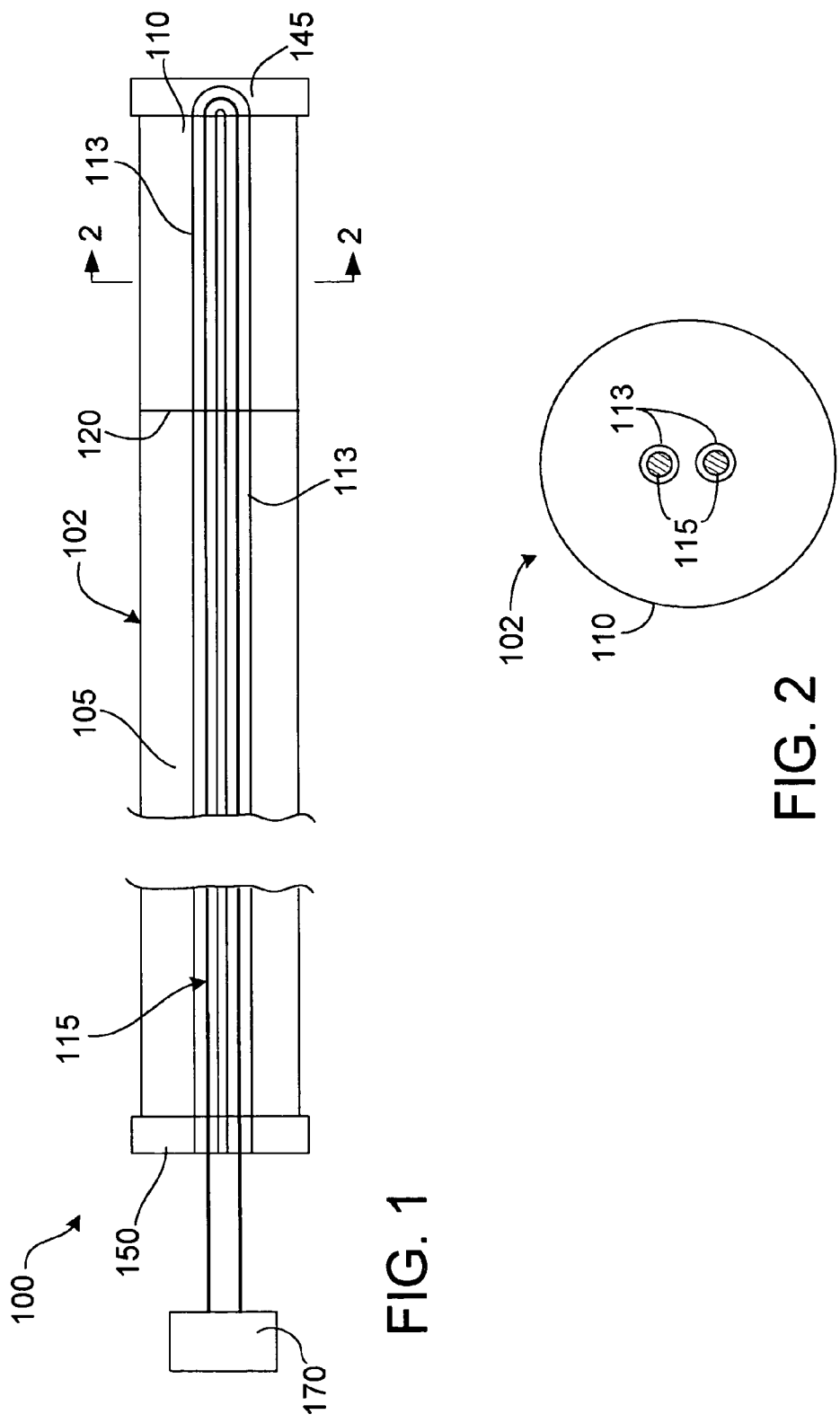

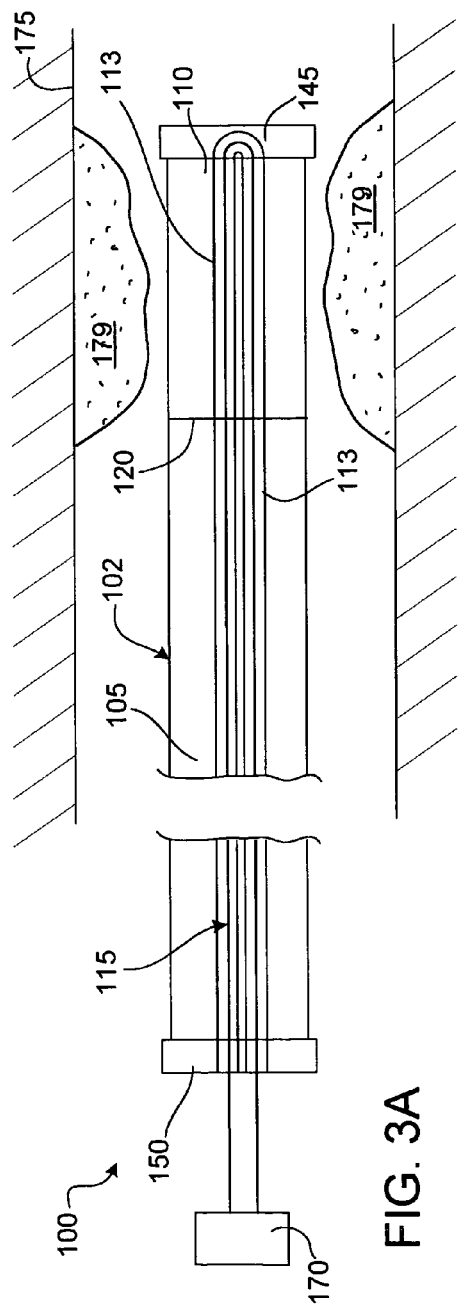
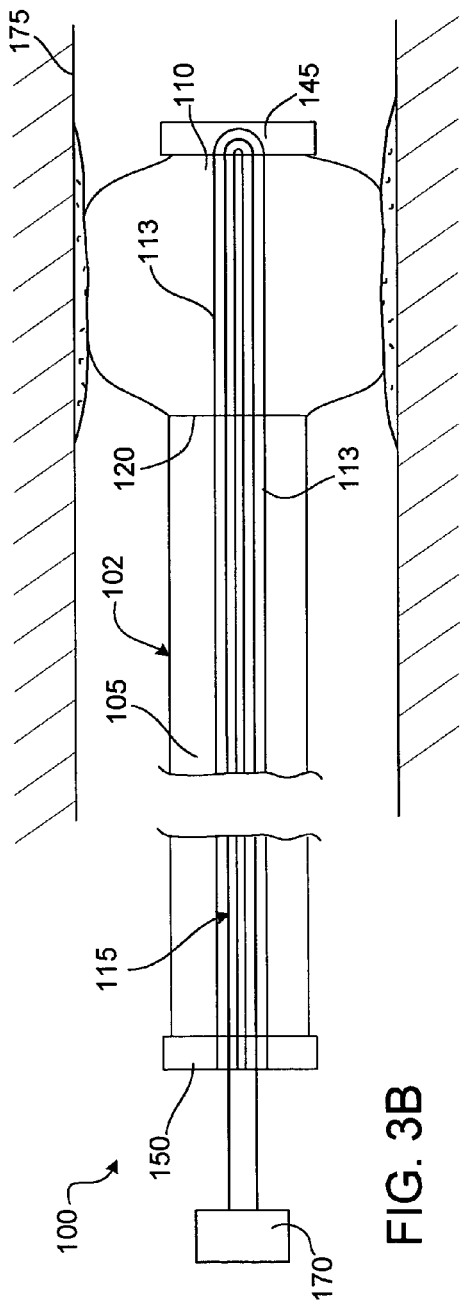

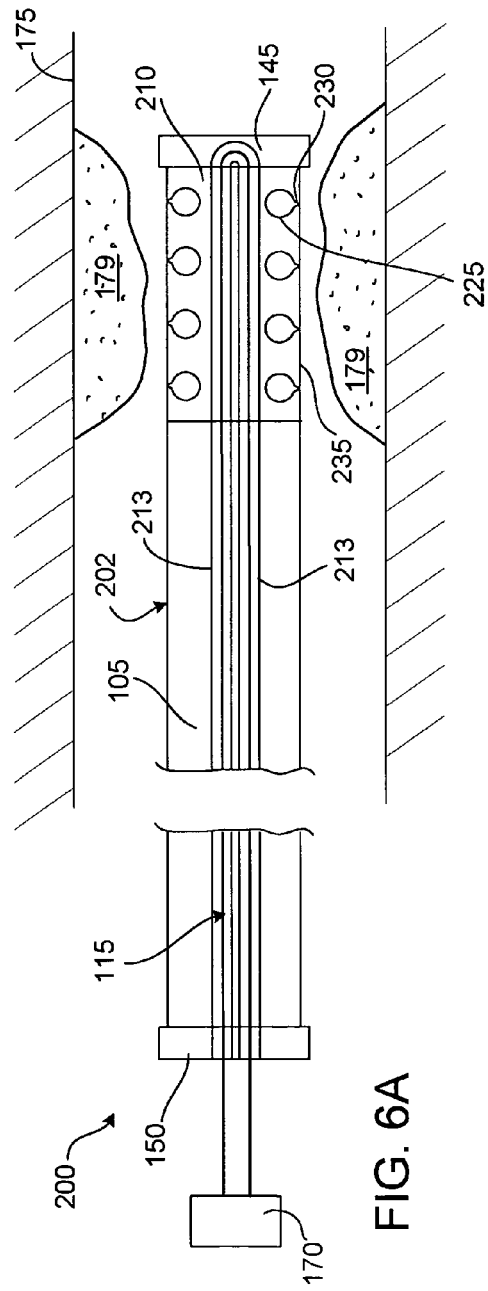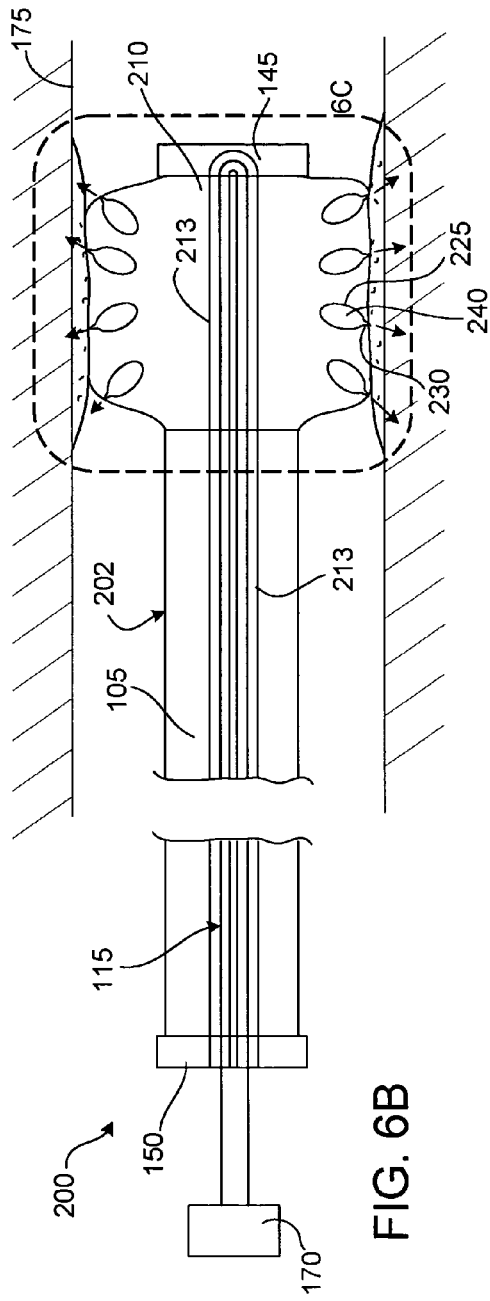

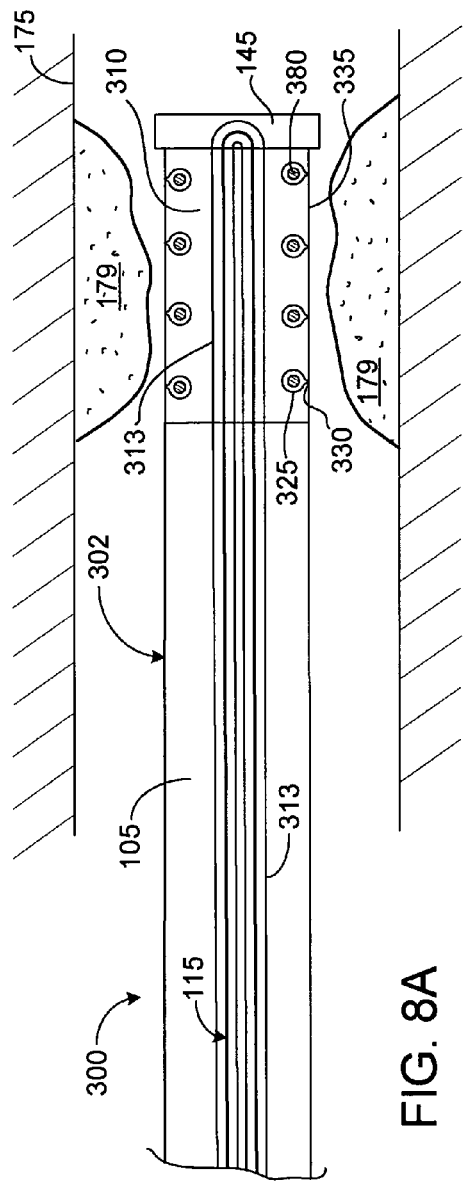
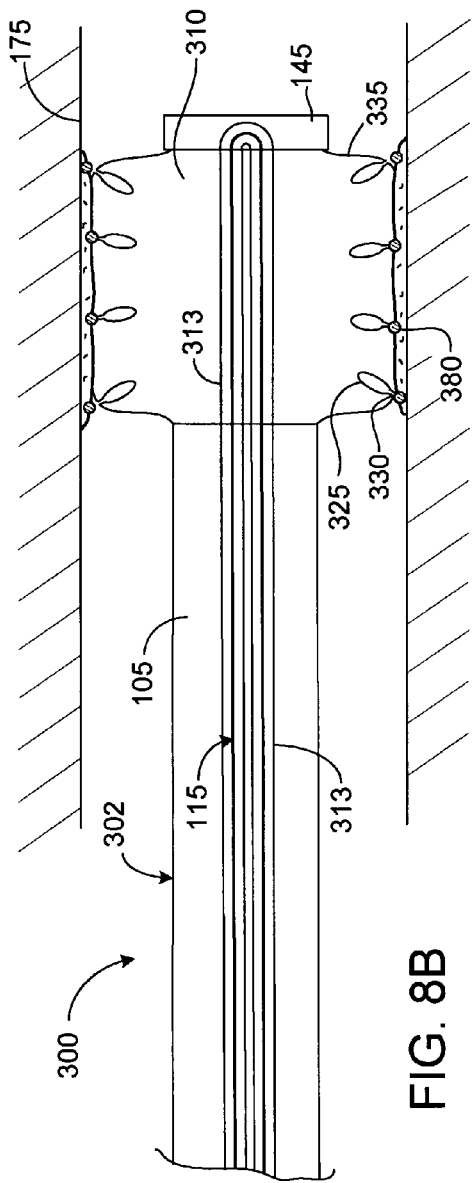
FIG. 8A
FIG. 8B

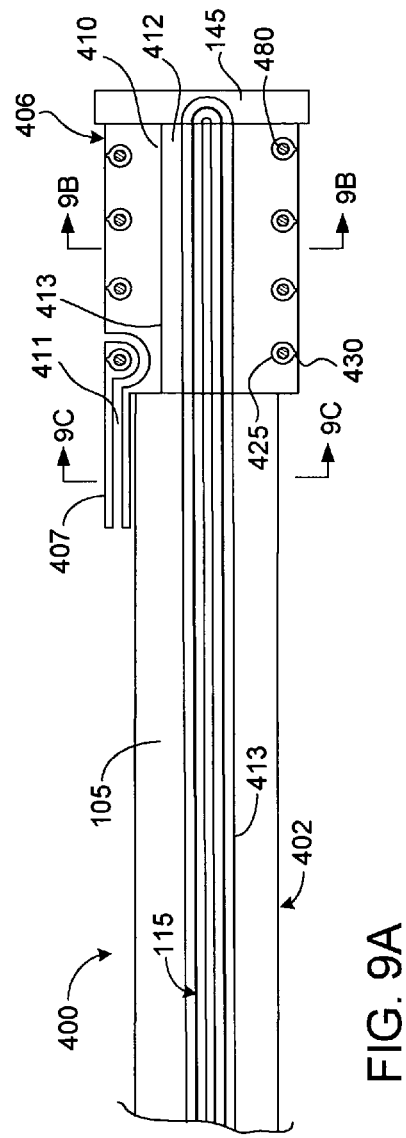
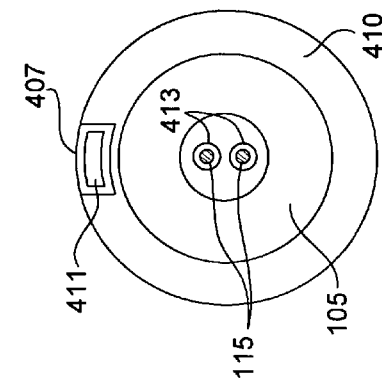
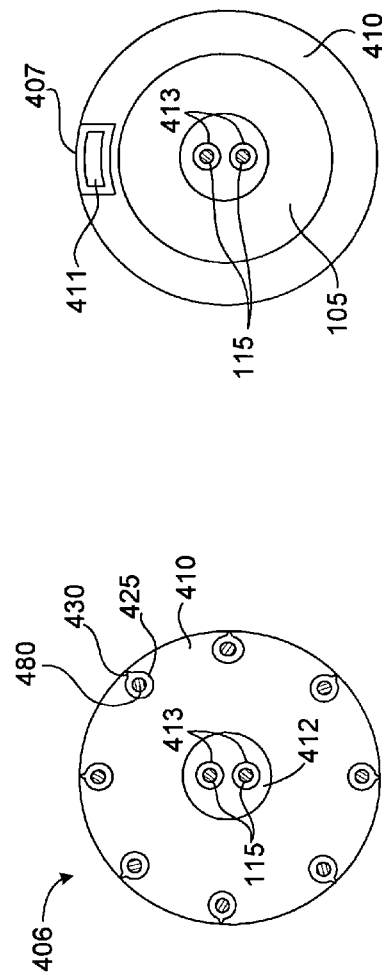

MEDICAL DEVICES AND RELATED METHODS

TECHNICAL FIELD

This invention relates to medical devices and related methods.

BACKGROUND

Systems are known for delivering medical devices, such as stents, into a body lumen. Often, such systems include a proximal portion that remains outside the body during use and a distal portion that is disposed within the body during use. The proximal portion typically includes a handle that is held by an operator of the system (e.g., a physician) during use, and the distal portion can include an outer tube surrounding an inner tube with a stent positioned therebetween. Generally, the operator of the system positions the distal portion within the lumen at a desired location (e.g., so that the stent is adjacent an occlusion). The operator can then retract the outer tube to allow the stent to engage the occlusion/lumen wall. The operator subsequently removes the distal portion of the system from the lumen.

SUMMARY

In general, the invention relates to medical devices, that include one or more expandable regions, as well as related systems and methods. The medical systems, for example, can be used to treat an occluded or partially occluded bodily vessel (e.g., blood vessel), to deliver a therapeutic agent at a desired location within a lumen of a subject (e.g., a blood vessel of a human), and/or to deliver an endoprosthesis (e.g., a stent) at a desired location within a lumen of a subject (e.g., a blood vessel of a human).

The medical devices generally include an elongate element (e.g., a wire including a shape-memory material, such as nickel-titanium alloy) that is configured to change in length (e.g., to contract) upon being exposed to certain forms of energy, such as electrical energy and/or thermal energy. The medical devices also generally include an expandable member (e.g., a portion of a catheter, a portion of an inner and/or outer member of an endoprosthesis delivery system, a portion of a sheath). The expandable member can be configured to expand as the elongate element contracts.

In some embodiments, the expandable member defines apertures that can contain a therapeutic agent. The therapeutic agent can be released from the expandable member when the expandable member is expanded in some cases.

In certain embodiments, the expandable member carries an endoprosthesis (e.g., a stent). The endoprosthesis can be deployed and/or released from the expandable member when the expandable member is expanded in many cases.

In some embodiments, an endoprosthesis (e.g., struts of the endoprosthesis) is retained within apertures defined by the expandable member. The endoprosthesis can be released from the apertures of the expandable member when the expandable member is expanded in certain cases.

In certain embodiments, the expandable member is positioned adjacent an inner surface of a medical balloon so that the expandable member creates a seal with the medical balloon when the expandable member is expanded.

Embodiments can include one or more of the following advantages.

In some embodiments, the medical systems can have a relatively low profile. This can, for example, allow the medical systems to be navigated through relatively narrow regions (e.g., relatively narrow bodily vessels) of a subject.

In certain embodiments, the medical systems can be operated by applying energy (e.g., electrical and/or thermal energy) to the elongate element of the medical systems. This can, for example, reduce the physical effort required on the part of the user to expand members of the medical systems.

In certain embodiments, the expandable members of the medical systems can be rotatable with respect to one or more other portions of the medical systems. In such embodiments, the rotatable expandable members can be used, for example, to help properly align an endoprosthesis (e.g., a bifurcation stent) within a bodily vessel of the subject.

In some embodiments, the medical systems include expandable members configured to form a seal with medical balloons (e.g., rotatable medical balloons). The expandable members, for example, can help to prevent leakage of inflation fluid from the medical balloons.

In certain embodiments, the expandable members of the medical systems can be constructed to expand asymmetrically.

In some embodiments, outer members (e.g., sheaths) of the medical systems can be constructed to expand radially. Thus, the medical systems can provide a more controlled delivery of endoprostheses. The medical systems, for example, can improve the accuracy and/or precision with which the endoprostheses are delivered.

Other features and advantages are within the description, the drawings, and the claims.

DESCRIPTION OF DRAWINGS

FIG. 1 is a broken cross-sectional view of an embodiment of a medical system having an expandable member.

FIG. 2 is a cross-sectional view of the medical system of FIG. 1 taken along line 2-2.

FIGS. 3A and 3B illustrate an embodiment of a method of using the medical system of FIG. 1.

FIGS. 6A and 6B illustrate an embodiment of a method of using the medical system of FIG. 4.

FIGS. 8A and 8B illustrate an embodiment of a method of using the medical system of FIG. 7.

FIG. 9A is a partial cross-sectional view of an embodiment of a medical system including a rotatable, expandable member retaining an endoprosthesis.

FIG. 9B is a cross-sectional view of the medical system of FIG. 9A taken along line 9B-9B.

FIG. 9C is a cross-sectional view of the medical system of FIG. 9A taken along line 9C-9C.

DETAILED DESCRIPTION

Elongate Member with an Expandable Member

Figure 4:
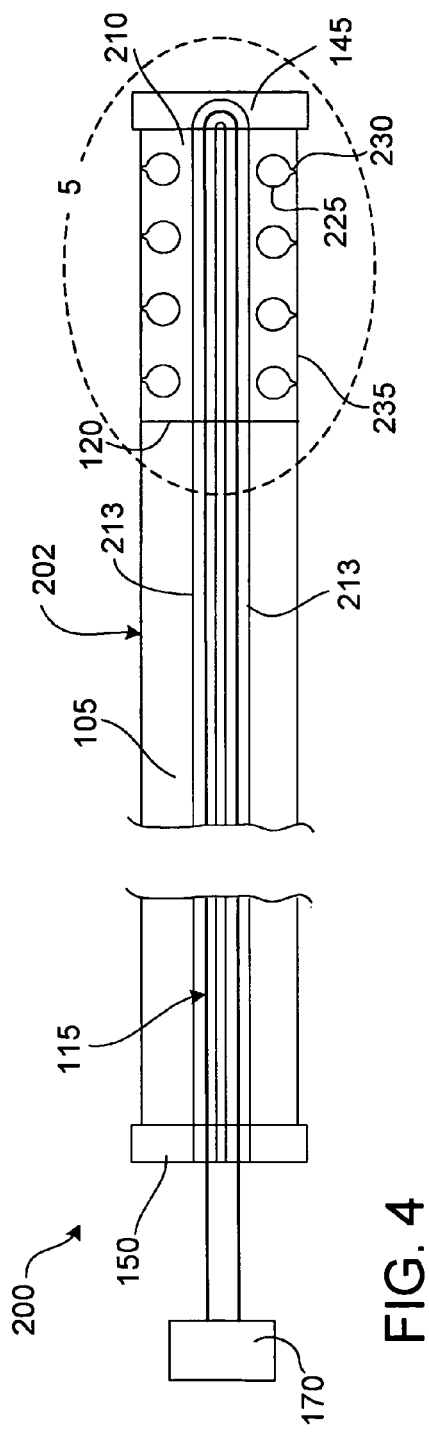
FIG. 4 is a broken cross-sectional view of an embodiment of a medical system including an expandable member retaining a therapeutic agent.

FIG. 1 shows a medical system 100 including an elongate member 102 disposed between end caps 145 and 150. Elongate member 102 includes a proximal, relatively rigid portion 105 and a distal, relatively compliant portion 110. As shown in FIG. 2, medical system 100 also includes a wire 115 disposed within a lumen 113 extending through elongate member 102. An energy source 170 is electrically connected to wire 115 at a proximal end of system 100.

FIGS. 3A and 3B illustrate a method of using system 100. The method includes introducing distal portion 110 of system 100 into a blood vessel 175, and directing distal portion 110 to a desired region within blood vessel 175 (e.g., a partially occluded region 179 of blood vessel 175). Once distal portion 110 is positioned in occluded region 179 of blood vessel 175, the user activates energy source 170 to apply a voltage across wire 115, causing a current to run through wire 115. As a result, wire 115 contracts. Because distal portion 110 of elongate member 102 is more compliant than proximal region 105 of elongate member 102, distal portion 110 expands radially under the contractive force of wire 115, while the dimensions of proximal portion 105 remain substantially unchanged (FIG. 3B). The expansion of distal portion 110 can help to dilate occluded region 179, which can help to improve blood flow through blood vessel 175. The user can subsequently deactivate energy source 170, allowing wire 115 and distal portion 110 to substantially return to their respective original dimensions. Alternatively, the current running through wire 115 can be increased to burn through (e.g., break) wire 115. As a result, wire 115 and distal portion 110 can substantially return to their original dimensions.

Referring again to FIG. 2, wire 115 extends substantially along a central axis of elongate member 102 (e.g., distal portion 110 of elongate member 102). This arrangement can help to promote symmetric compression, and thus symmetric expansion, of distal portion 110. Wire 115 is movably positioned within lumen 113 of elongate member 102. Lumen 113 is formed of multiple channels that extend through proximal portion 105, distal portion 110, and end caps 145 and 150 of elongate member 102. As described below, these portions of elongate member 102 are positioned such that the channels of the various portions are aligned with one another to form lumen 113, which extends from a proximal end of elongate member 102 to a distal end region of elongate member 102 and loops back to the proximal end of elongate member 102. The channels can have a slightly greater diameter than wire 115 such that wire 115 is free to move within lumen 113. Wire 115 can be attached to both distal end cap 145 and proximal end cap 150. Any of various attachment techniques can be used to attach wire 115 to the end caps. Examples of suitable attachment techniques include adhesive, welding, and bonding techniques.

The amount of contraction of wire 115 can be a function of various factors, such as the material from which wire 115 is formed, the size (e.g., length and diameter) of wire 115, the voltage applied across wire 115, the electrical current that passes through wire 115, and/or the temperature of wire 115. Generally, as one or more of these parameters increase, the amount of contraction of wire 115 also increases.

In some embodiments, wire 115 is formed of one or more materials that contract when heated. Alternatively or additionally, wire 115 can be formed of any of various materials that contract in response to having a voltage applied across them. In certain embodiments, wire 115 is formed of a shape-memory material, such as nickel-titanium alloy (e.g., Flexinol®, manufactured by Dynalloy, Inc. of Costa Mesa, Calif.). Wire 115 can alternatively or additionally be formed of any of various other shape-memory materials. Examples of shape-memory materials include metal alloys, such as nitinol (e.g., 55% nickel, 45% titanium), silver-cadmium (Ag—Cd), gold-cadmium (Au—Cd), gold-copper-zinc (Au—Cu—Zn), copper-aluminum-nickel (Cu—Al—Ni), copper-gold-zinc (Cu—Au—Zn), copper-zinc/(Cu—Zn), copper-zinc-aluminum (Cu—Zn—Al), copper-zinc-tin (Cu—Zn—Sn), copper-zinc-xenon (Cu—Zn—Xe), iron beryllium (Fe3Be), iron platinum (Fe3Pt), indium-thallium (In—Tl), iron-manganese (Fe—Mn), nickel-titanium-vanadium (Ni—Ti—V), iron-nickel-titanium-cobalt (Fe—Ni—Ti—Co) and copper-tin (Cu—Sn). See, e.g., Schetsky, L. McDonald, "Shape Memory Alloys", Encyclopedia of Chemical Technology (3rd ed.), John Wiley & Sons, 1982, vol. 20. pp. 726-736.

Generally, the dimensions of wire 115 can be selected as desired. For example, the dimensions of wire 115 can be selected to expand distal portion 110 to a desired level. In some embodiments, wire 115 has a diameter of 0.90 millimeter (e.g., 0.75 millimeter, 0.65 millimeter, 0.50 millimeter, 0.35 millimeter, 0.25 millimeter, 0.15 millimeter, 0.05 millimeter) or less and/or 0.03 millimeter (e.g., 0.05 millimeter, 0.15 millimeter, 0.25 millimeter, 0.35 millimeter, 0.50 millimeter, 0.65 millimeter, 0.75 millimeter) or more. In certain embodiments, wire 115 has a length of about 25 millimeters (e.g., about 15 centimeters, about 25 centimeters, about 40 centimeters, about 50 centimeters, about 65 centimeters, about 75 centimeters) or more and/or about 90 centimeters (e.g., about 75 centimeters, about 65 centimeters, about 50 centimeters, about 40 centimeters, about 25 centimeters, about 15 centimeters) or less.

The energy source 170 can apply a voltage of 0.2 volts to about ten volts across wire 115. Similarly, energy source 170 can pass a current of 0.01 amps to about 0.5 amps through wire 115.

The temperature of wire 115, in response to having voltage applied across it, can increase by about ten degrees Celsius to about 70 degrees Celsius (e.g., about ten degrees Celsius to about 50 degrees Celsius, about 50 degrees Celsius to about 70 degrees Celsius). The temperature of wire 115, for example, can range from about 37 degrees Celsius to about 110 degrees Celsius while the energy is being applied to it or shortly thereafter.

In some embodiments, wire 115 contracts by about 0.1 percent (e.g., about 0.4 percent, about 0.7 percent, about one percent, about two percent, about three percent, about four percent, about five percent, about six percent, about seven percent, about eight percent, about nine percent, about ten percent) or more. Wire 115 can, for example, contract by about 0.1 percent to about ten percent (e.g., about one percent to about ten percent, about 0.1 percent to about four percent, about three percent to about five percent) of its total length prior to having a voltage applied across it.

Proximal portion 105 of elongate member 102 can be a substantially solid, cylindrical member including channels that partially form lumen 113. In some embodiments, proximal portion 105 is formed of one or more relatively rigid materials. In certain embodiments, proximal portion 105 is formed of one or more materials that are relatively good insulators, which can reduce heat loss to the surrounding environment (e.g., to blood vessel 175) during use. This can allow for a relatively efficient use of energy to contract wire 115. Examples of materials from which proximal portion 105 can be formed include polytetrafluoroethylene (e.g., Teflon®), polyether-block co-polyamide polymers (e.g., PEBAX® 70D and/or PEBAX® 72D), copolyester elastomers (e.g., Arnitel® copolyester elastomers), thermoplastic polyester elastomers (e.g., Hytrel®), thermoplastic polyurethane elastomers (e.g., Pellethane™), polyeolefins (e.g., Marlex® polyethylene, Marlex® polypropylene), high-density polyethylene (HDPE), low-density polyethylene (LDPE), polyamides (e.g., Vestamid®), and combinations of these materials. Proximal portion 105 can be formed using any of various methods, such as extrusion methods, injection molding methods, and/or dip coating methods.

In certain embodiments, proximal portion 105 includes a spring steel spiral that extends along its length. The spring steel spiral can, for example, help to increase the rigidity of proximal portion 105. In some embodiments, the spring steel spiral is encapsulated within the body of proximal portion 105. The spring steel spiral can, for example, be positioned about the circumference of a first tubular member and coated with a coating material to form proximal portion 105. Alternatively or additionally, the spring steel spiral can be extruded along with the material with which proximal portion 105 is formed.

Distal portion 110 of elongate member 102 can also be a generally solid, cylindrical member including channels that partially form lumen 113. In some embodiments, distal portion 110 is formed of one or more relatively compliant materials. In certain embodiments, distal portion 110 is formed of one or more materials that are relatively good insulators. Examples of materials from which distal portion 110 can be formed include silicone, polyether-block co-polyamide polymers (e.g., PEBAX® 25D and/or PEBAX® 40D), polyesters (e.g., Hytrel® and/or Amitel®), polysulfones (PSO), polytetramethylene glycol (PTMG), and polyurethanes (e.g., Tecothane®). Distal portion 110 can be formed using any of various techniques, such as extrusion techniques, injection molding techniques, and/or dip coating techniques. Proximal portion 105 can be attached to distal portion 110 at a proximal end 120 of distal portion 110. Any suitable technique can be used to attach proximal portion 105 and distal portion 110. Proximal portion 105 and distal portion 110 can, for example, be joined with a butt weld, a lap weld, a laser weld, a bond, and/or adhesive.

As noted above, proximal portion 105 is generally more rigid than proximal portion 110. In some embodiments, the Young's modulus of proximal portion 105 is at least about five (e.g., ten, 15, 20, 25, 50, 75, 100) times greater than the Young's modulus of distal portion 110.

In general, end caps 145, 150 are formed of a material that is more rigid than the relatively compliant material from which distal portion 110 of elongate member 102 is formed. For example, end caps 145, 150 can be formed of polytetrafluoroethylene (e.g., Teflon®), polyether-block co-polyamide polymers (e.g., PEBA® 70D and/or PEBAX® 72D), copolyester elastomers (e.g., Arnitel® copolyester elastomers), thermoplastic polyester elastomers (e.g., Hytrel®), thermoplastic polyurethane elastomers (e.g., Pellethane™), polyeolefins (e.g., Marlex® polyethylene, Marlex® polypropylene), high-density polyethylene (HDPE), low-density polyethylene (LDPE), polyamides (e.g., Vestamid®), polycarbonate, epoxy, polyurethane, or combinations of these materials. End caps 145 and 150 can be formed using any of various techniques, such as extrusion techniques, injection molding techniques, and/or dip coating techniques. As shown in FIG. 1, distal end cap 145 is attached to distal portion 110, and proximal end cap 150 is attached to rigid member 105. Any suitable technique can be used to attach end caps 145, 150 to rigid member 105 and distal portion 110, respectively. Examples of suitable techniques include adhesive, welding, and bonding techniques.

Elongate member 102 can be assembled using any of various methods. As an example, after forming proximal portion 105 and distal portion 110, portions 105 and 110 can be positioned to longitudinally abut one another such that the channels of proximal portion 105 are aligned with the channels of distal portion 100 to partially form lumen 113. Proximal and distal portions 105 and 110 can be held in this abutted position with one or more pins extending through the channels, and can be attached to one another using any of the techniques described above. After portions 105 and 110 have been attached to one another, end caps 145 and 150 can be attached to proximal portion 105 and distal portion 110, respectively, such that channels extending through end caps 145 and 150 are aligned with the channels of proximal and distal portions 105 and 110 to form lumen 113. End caps 145 and 150 can be attached to proximal and distal portions 105 and 110 using any of the techniques described above for attaching proximal portion 105 to distal portion 110. The pins can then be removed from lumen 113, and wire 115 can be positioned within lumen 113, as shown in FIG. 1. Wire 115 can then be attached to end caps 145 and 150 using any of the methods described above.

In certain embodiments, an endoprosthesis is carried by distal portion 110 of elongate member 102. Examples of endoprostheses include stents (e.g., self-expanding stents and balloon expandable stents) and vena cava filters. Examples of stents include bifurcation stents, AAA stents, ear canal stents, prostate stents, and uterine stents. In such embodiments, distal portion 110 of elongate member 102 can be used to deliver and/or deploy (e.g., by expanding distal portion 110) the endoprosthesis within blood vessel 175 of the subject.

Elongate Member with an Expandable Member Containing a Therapeutic Agent

Figure 5:
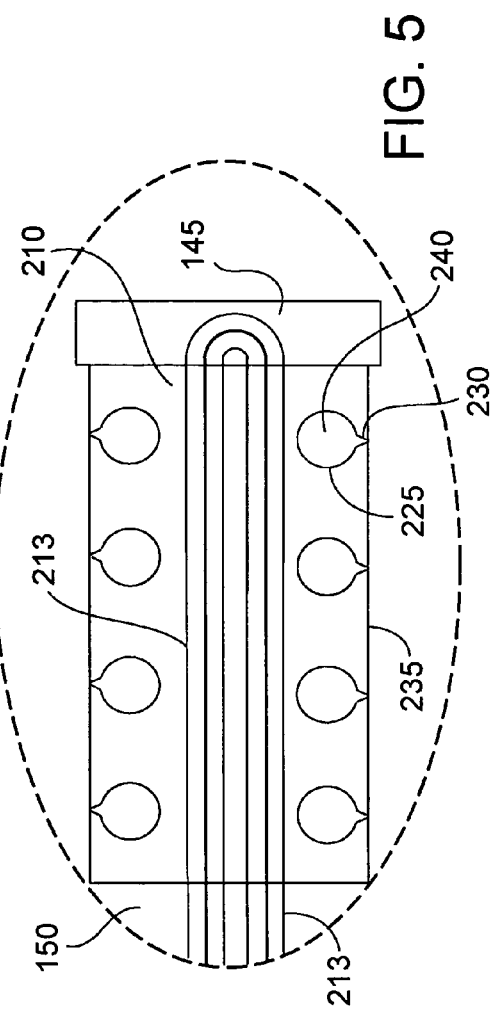
FIG. 5 is an enlarged view of region 5 in FIG. 4.

In some embodiments, the distal portion of the elongate member can be configured to contain a therapeutic agent that can be released when the distal portion is expanded. As shown in FIGS. 4 and 5, for example, a medical system 200 includes an elongate member having a distal portion 210 that defines multiple apertures 225. Distal portion 210 further defines multiple slots 230 that extend from the apertures to an outer surface 235 of distal portion 210. A liquid therapeutic agent 240, such as paclitaxel, is contained within apertures 225. Apertures 225 can be sized to contain a desired amount of therapeutic agent 240, and slots 230 can be sized to prevent the therapeutic agent from escaping form distal portion 210 while distal portion 210 is in an unexpanded state.

Figure 6C:
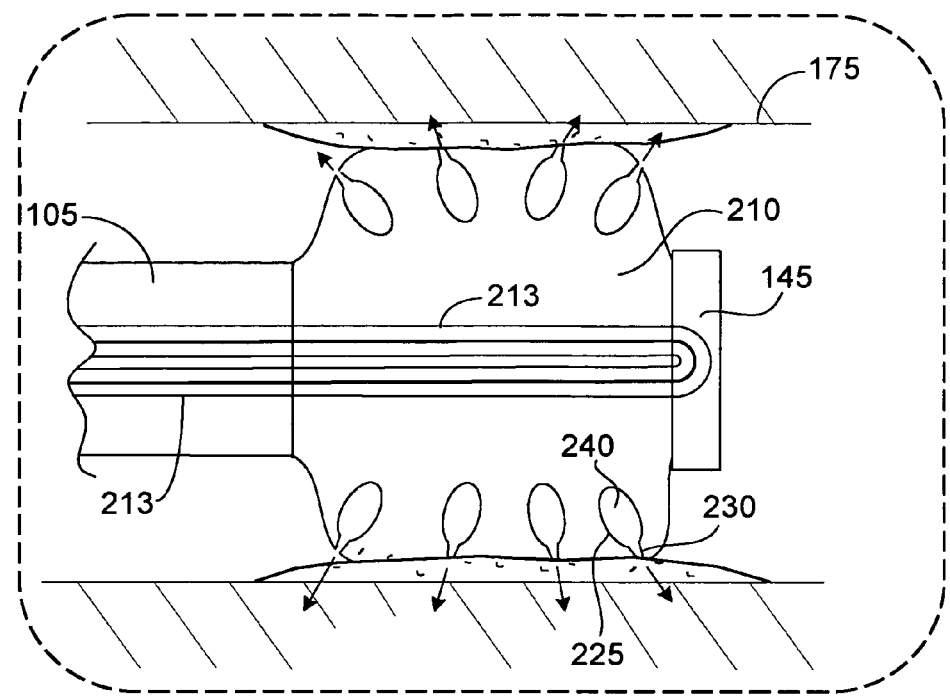
FIG. 6C is an enlarged view of region 6C in FIG. 6B.

FIGS. 6A-6C illustrate a method of delivering therapeutic agent 240 to a desired region of blood vessel 175 of the subject. In a similar manner to the method described above with respect to FIGS. 3A and 3B, distal portion 210 is positioned within the desired region of blood vessel 175. Subsequently, the user activates energy source 170, causing wire 115 to contract, which causes distal portion 210 to expand and release therapeutic agent 240, as shown in FIGS. 6B and 6C.

Referring to FIGS. 6B and 6C, apertures 225 and slots 230 change in size and/or shape as distal portion 210 expands. For example, apertures 225 can become more elongated, and slots 230 can increase in width. Opposite edges of slots 230 can become spaced apart from one another, thereby forming a passageway through which therapeutic agent 240 can escape from apertures 225. As a result of the changed size and shape of apertures 225 and slots 230 and/or the pressure created within apertures 225 by the compression of distal portion 210, therapeutic agent 240 is released (e.g., ejected) from distal portion 210, delivering therapeutic agent 240 within blood vessel 175.

After delivering therapeutic agent 240, elongate member 202 can be returned to its original dimensions using any of the various techniques described above, and the user can remove system 200 from blood vessel 175 of the subject.

Apertures 225 and slots 230 can be formed within distal portion 210 using any of various techniques, such as laser ablation and/or microengraving. In certain embodiments, depressions are formed within an outer surface of a member (e.g., the distal portion of the elongate member). Subsequently, a material (e.g., a relatively soft material) is applied to the outer surface of the member over the depressions to form apertures 225. Slots 230 are then formed in the soft material to provide access from apertures 225 to an outer surface 235 of the member.

In some embodiments, distal portion 210 is formed by making first and second tubes formed of a relatively soft material (e.g., polyurethane, such as Tecothane® 74A). The inner diameter of the second tube is formed to be slightly smaller than the outer diameter of the first tube. Blind holes can be formed (e.g., laser ablated) into the outer surface of the first tube, forming apertures 225. The blind holes can, for example, be formed to have a diameter of about 20 micrometers and a depth of about 60 micrometers. Chloroform can then be applied to the second tube, causing the second tube to swell (e.g., to swell up to about 900 percent of its original size). The second tube can then be placed over the first tube, and holes can be formed in the wall of the second tube. The holes in the second tube can be aligned with the holes of the first tube. The chloroform can then be removed from the second tube, causing the second tube to shrink tightly around the first tube. This can also cause the holes in the second tube to shrink, forming slots 230, which can have a diameter of about two micrometers.

Apertures 225 and slots 230 can alternatively or additionally be formed in distal portion 210 using injection molding techniques. As an example, a tube can be injection molded to include silica microparticles. The tube can be formed of a relatively soft material (e.g., polyurethane, such as Tecothane® 74A). The silica microparticles can be positioned in those regions of the tube in which apertures 225 and slots 230 are desired. Holes having a diameter smaller than the diameter of the silica microparticles can be formed in the tube to lead from the outer surface of the tube to the silica microparticles positioned therein. The holes can, for example, have a diameter of about two microns. The holes can be formed using any of various techniques, such as laser ablation, drilling, and/or needling. After forming the holes, chloroform can be applied to the tube, causing the tube to swell. The microparticles can be removed through the holes using a suction device. The chloroform can then be removed, causing the tube to shrink. As a result of this process, the region in which the microparticles were positioned in the tube can define apertures 225, and the holes through which the microparticles were removed can define slots 230.

In certain embodiments, distal portion 210 is formed of a porous material, such as porous silicon (e.g., Biosilicon®), poly(styrenedivinylbenzene), or sponge. In such embodiments, the pores of the material can contain a therapeutic agent, and the therapeutic agent can be ejected from the distal portion 210 upon expansion of distal portion 210. The pores can be provided as an alternative to or in addition to apertures 225.

Figure 20:
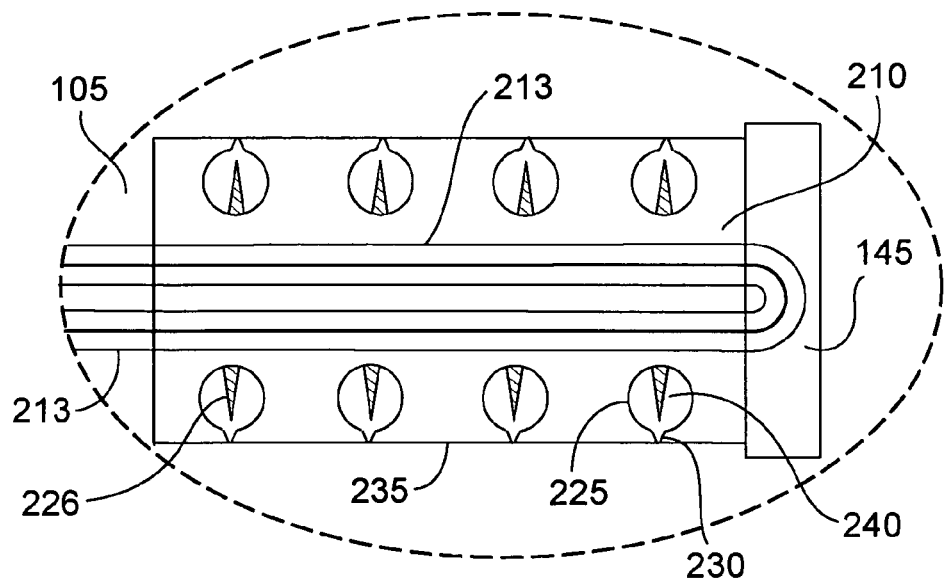
FIG. 20 is a partial cross-sectional view of an embodiment of a medical system including an expandable member.

In some embodiments, as shown in FIG. 20, needles 226 are positioned within apertures 225 of distal portion 210. Needles 226 can be secured within apertures 225 using any of various suitable techniques, such as adhesive, welding, and/or bonding techniques. Needles 226 can be positioned within apertures 225 such that, when distal portion 210 is in an unexpanded state, needles 226 do not protrude beyond outer surface 235 of distal portion 210, and, when distal portion 210 is in an expanded state, needles 226 protrude beyond outer surface 235 of distal portion 210. When distal portion 210 is inserted into a bodily vessel (e.g., a blood vessel) and expanded, needles 226 can penetrate a side wall of the vessel. Needles 226 can, for example, be used to locally deliver a therapeutic agent to an interior region of blood vessel 175 or to a region of tissue surrounding blood vessel 175. Needles 226 can alternatively or additionally be used to apply electroporation to the interior region of blood vessel 175. For example, a pulsed potential can be applied to needles 226 during use in order to open cell pores of the vessel.

In certain embodiments, an endoprosthesis is carried by distal portion 210 of elongate member 202. In such embodiments, distal portion 210 of elongate member 202 can be used to deliver and/or deploy (e.g., by expanding distal portion 210) the endoprosthesis within blood vessel 175 of the subject.

Elongate Member with an Expandable Member Retaining an Endoprosthesis

Figure 7:
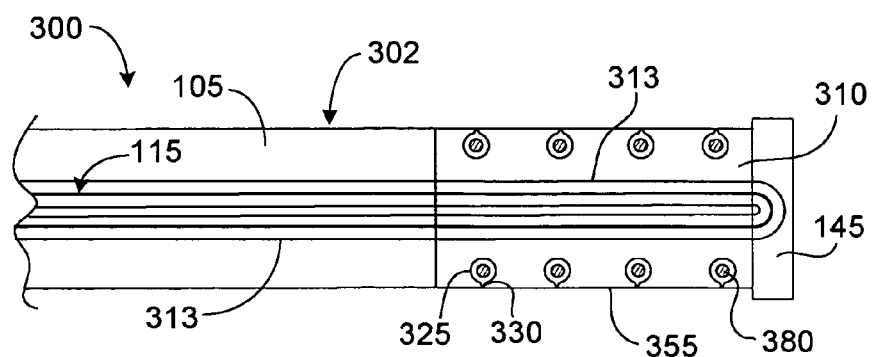
FIG. 7 is a partial cross-sectional view of an embodiment of a medical system including an expandable member retaining an endoprosthesis.

In some embodiments, an endoprosthesis (e.g., struts of an endoprosthesis) can be retained within the apertures formed in the distal region of the elongate member. Referring to FIG. 7, for example, struts of a stent 380 (e.g., a self-expanding stent) are retained within apertures 325 of distal portion 310. Apertures 325 are slightly larger than the struts of self-expanding stent 380 so that the struts can be completely retained therein. Slots 330 of distal portion 310 generally have a smaller width than the width or diameter of the struts of stent 380. Due to the size of slots 330, stent 380 is prevented from escaping from apertures 325 while distal portion 310 is in an unexpanded state.

During use, as shown in FIGS. 8A and 8B, distal portion 310 is introduced into blood vessel 175 and directed to a desired region of blood vessel 175. Distal portion 310 of elongate member 302 is subsequently expanded, causing apertures 325 and slots 330 to change shape to allow the release of stent 380 (FIG. 8B). After stent 380 has been released from apertures 325, distal portion 310 is returned to approximately its original dimensions and withdrawn from blood vessel 175, leaving self-expanding stent 380 implanted within blood vessel 175.

Apertures 325 and slots 330 can be formed using any of various methods. As an example, multiple channels, which roughly correspond to the dimensions of stent 380 (e.g., to the dimensions of the struts of stent 380) can be defined within an outer surface of a member (e.g., a distal portion of the elongate member). Subsequently, stent 380 (e.g., the struts of stent 380) can be positioned within the channels in an unexpanded state. After positioning stent 380 within the channels, an outer layer of material (e.g., a relatively soft material) can be applied to the outer surface of the member to substantially cover the channels to form apertures 325 in which stent 380 is retained. Slots 330, which lead from apertures 325 to an outer surface 335 of the member, can then be formed within the outer layer of material using any suitable technique.

As an alternative to or in addition to the arrangement described above, stent 380 can be prevented from escaping from apertures 325 by a compressive force applied to stent 380 by side walls of apertures 325. The width of apertures 325 can, for example, be smaller than the diameter of the struts of stent 380 such that a compressive force is applied to stent 380 when stent 380 is positioned within apertures 225 and distal portion 310 is in an unexpanded state. The width of apertures 325 can increase upon expanding distal portion 310 to release stent 380. In such embodiments, the apertures can be free of a top surface defining a slot.

In some embodiments, apertures 325 contain one or more therapeutic agents in addition to stent 380.

Elongate Member with a Rotatable, Expandable Member Retaining an Endoprosthesis

In certain embodiments, the medical systems include a rotatable, expandable member. For example, FIG. 9A shows a medical system 400 that is similar to system 300 described with respect to FIG. 7 above. System 400 includes an elongate member 402 disposed between a distal end cap 145 and a proximal end cap (not shown). Elongate member 402 has a relatively rigid, proximal portion 105 and a relatively compliant, distal portion 406. As shown in FIG. 9B, distal portion 406 includes a tubular, outer portion 410, which surrounds a substantially, cylindrical inner portion 412. Outer portion 410 is rotatably positioned about inner portion 412. Outer portion 410 and inner portion 412 are less rigid than proximal portion 105. A secondary guidewire housing 407 integrally extends in a proximal direction from outer portion 410. As shown in FIG. 9A-9C, secondary guidewire housing 407 and outer portion 410 define a lumen 411 that is configured to contain a secondary guidewire. An endoprosthesis 480 (e.g., a self-expanding stent having a relatively large opening in its sidewall) is retained within apertures 425 formed in outer portion 410. During use, the secondary guidewire can pass under a strut of endoprosthesis 480 and outwardly through the opening defined in the sidewall of endoprosthesis 480, as described below. Wire 115, as shown in FIGS. 9B and 9C, extends through a lumen 413 defined by elongate member 402 substantially along a central axis of the elongate member and is attached to the end caps. An energy source (not shown) is electrically connected to wire 115.

Figure 10A:
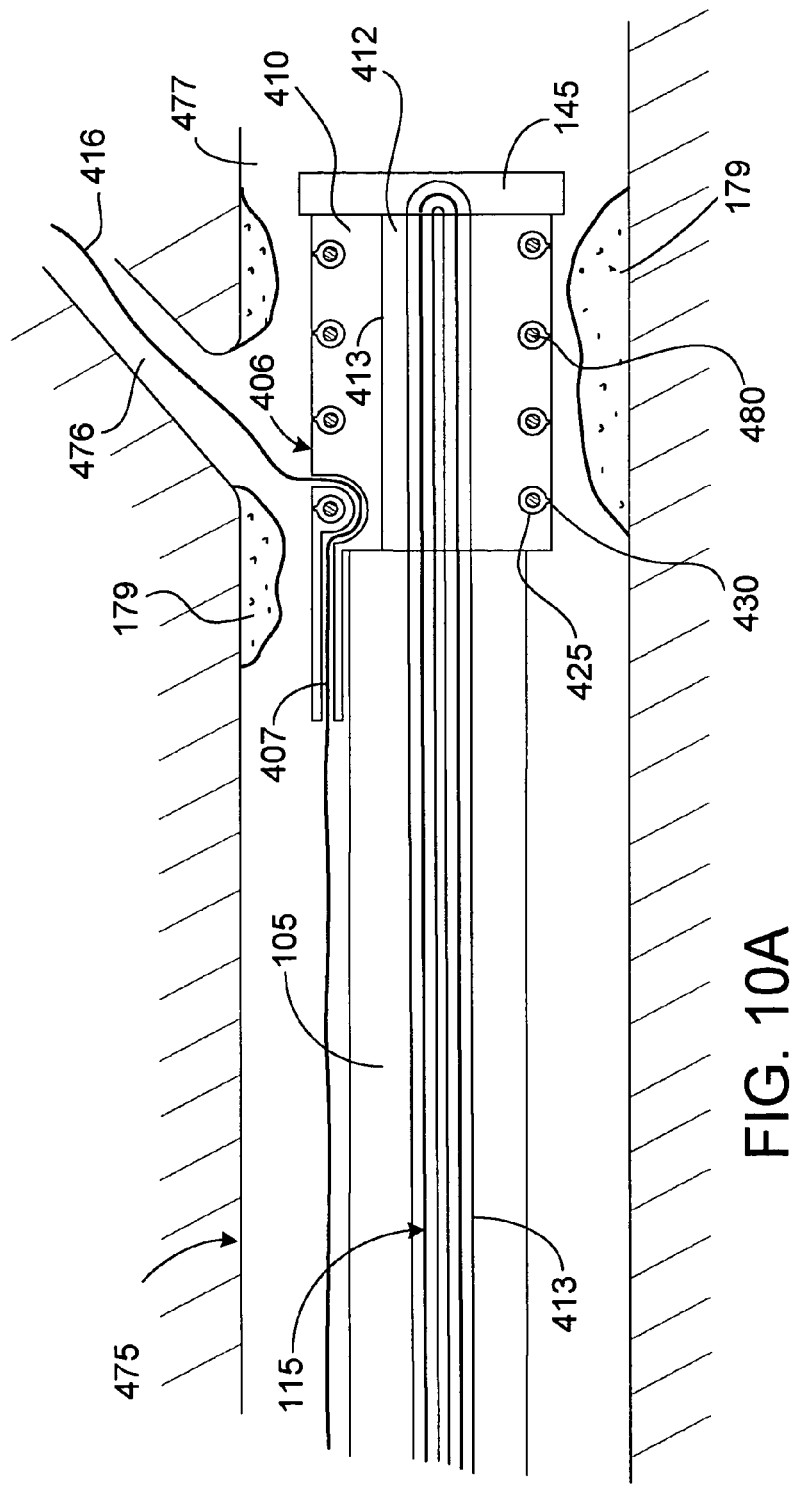
FIGS. 10A and 10B illustrate an embodiment of a method of using the medical system of FIG. 9A.
Figure 10B:
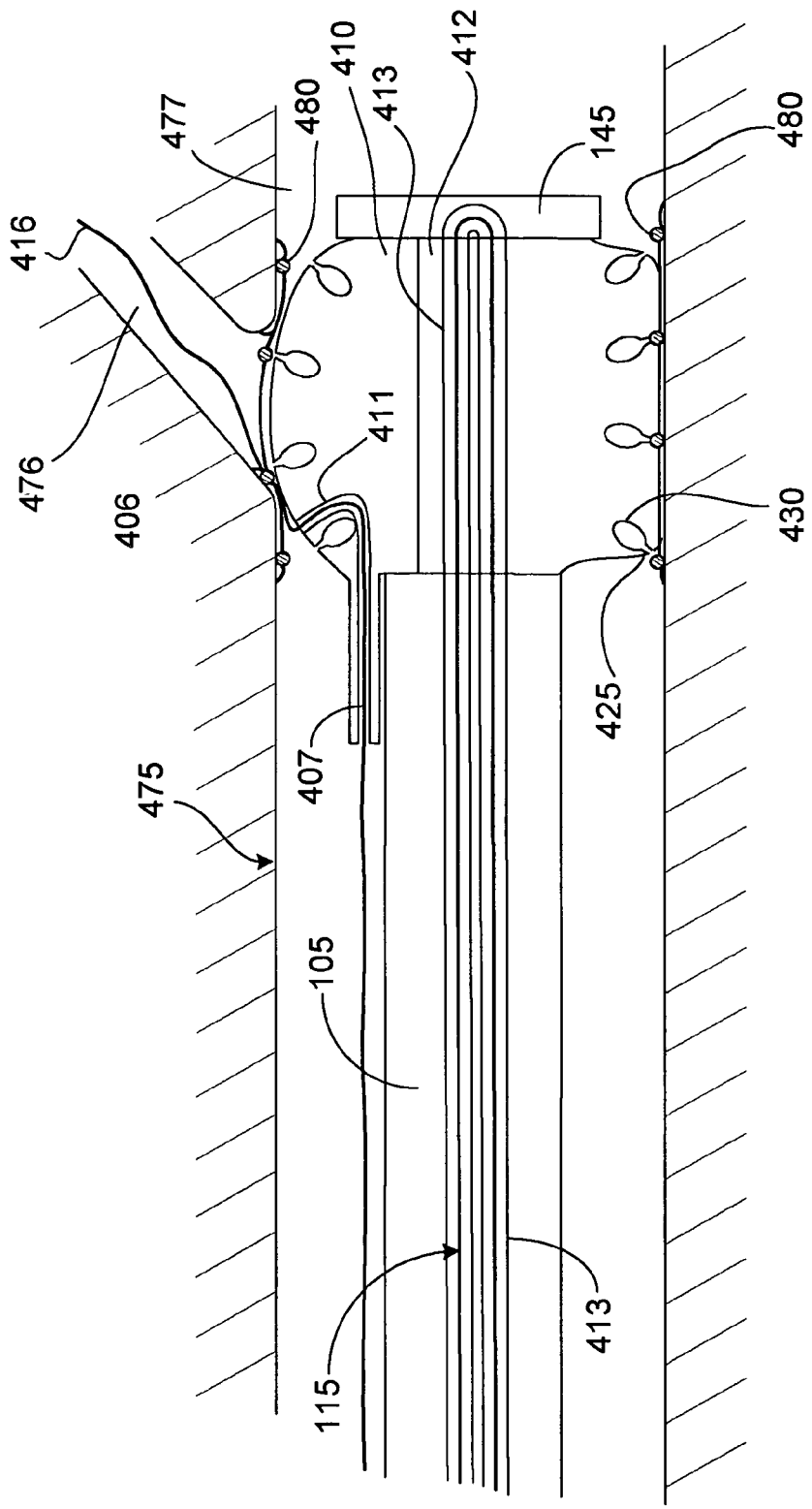

During use, a secondary guidewire 416 is positioned within a branch portion 476 of a blood vessel 475 of a subject, and a distal region of system 400 is introduced into blood vessel 475 over secondary guidewire 416, as shown in FIGS. 10A and 10B. As the distal region of system 400 is advanced through blood vessel 475, secondary guidewire 416 causes outer portion 410 to rotate about inner portion 412 until the side opening of stent 480, in which secondary guidewire 416 is positioned, becomes aligned with branch 476 of blood vessel 475.

Once outer portion 410 is positioned as desired within blood vessel 475, outer portion 410 is expanded to release stent 480, as shown in FIG. 10B. The side opening of stent 480 is substantially aligned with branch 476, which can help to reduce obstruction of blood flow through branch 476. Outer portion 410 can be expanded using a technique similar to those discussed in the above-described embodiments (e.g., by activating the energy source). After stent 480 has been released, elongate member 402 (e.g., outer portion 410 and inner portion 412 of elongate member 402) can be approximately returned to its original dimensions using any of the various techniques described above, and elongate member 402 can be withdrawn from blood vessel 475 of the subject, leaving stent 480 implanted within the blood vessel.

As noted above, outer portion 410 can be configured to rotate about inner portion 412. Outer portion 410 is a tubular member that has an inner diameter that is larger than the outer diameter of inner portion 412. As a result, outer portion 410 can freely rotate about inner portion 412. Both inner portion 412 and outer portion 410 are positioned between the relatively rigid, proximal portion 105 and distal end cap 145. Thus, inner portion 412 and outer portion 410 can be prevented from being axially displaced when wire 115 contracts. Outer portion 410 and/or inner portion 412 of distal portion 406 can be formed of any of the various relatively compliant materials described herein with respect to distal portion 110 of FIG. 1.

In certain embodiments, secondary guidewire housing 407 is formed of the same material as outer portion 410. Secondary guidewire housing 407, for example, can be integrally formed with outer portion 410. In some embodiments, secondary guidewire housing 407 and outer portion 410 are formed separately and subsequently attached to one another. Secondary guidewire housing 407 can be formed of any of various materials having a rigidity sufficient to rotate outer portion 410 without permanent deformation or damage. Examples of such materials include nylon 12, polyethylene terephthalate (PET), and polyimide.

In some embodiments, one or more low friction materials are disposed between the outer surface of inner portion 412 and the inner surface of outer portion 410. The low friction material(s) can be any of various materials capable of reducing rotational friction between inner portion 412 and outer portion 410. Examples of such materials include hydrogel, silicon, fluorinated inorganic hybrid polymer, fluorinated organic hybrid polymer, and Bioslide® available from Boston Scientific SciMed, Inc. of Maple Grove, Minn.

In certain embodiments, the relatively rigid, proximal portion 105 includes a recessed region (not shown) that is sized to receive at least a proximal region of inner portion 412 as wire 115 contracts. In such embodiments, the compression forces created between distal end cap 145 and proximal portion 105 can act primarily on outer portion 410. Thus, the efficiency with which outer portion 410 is expanded can be improved.

Apertures 425 can be formed within outer portion 410 and stent 480 can be positioned within apertures 425 using methods similar to those discussed above with respect to apertures 325 and stent 380 of system 300 of FIG. 7. In some embodiments, apertures 425 contain one or more therapeutic agents in addition to stent 480.

Medical System Including a Rotatable Medical Balloon

Figure 11:
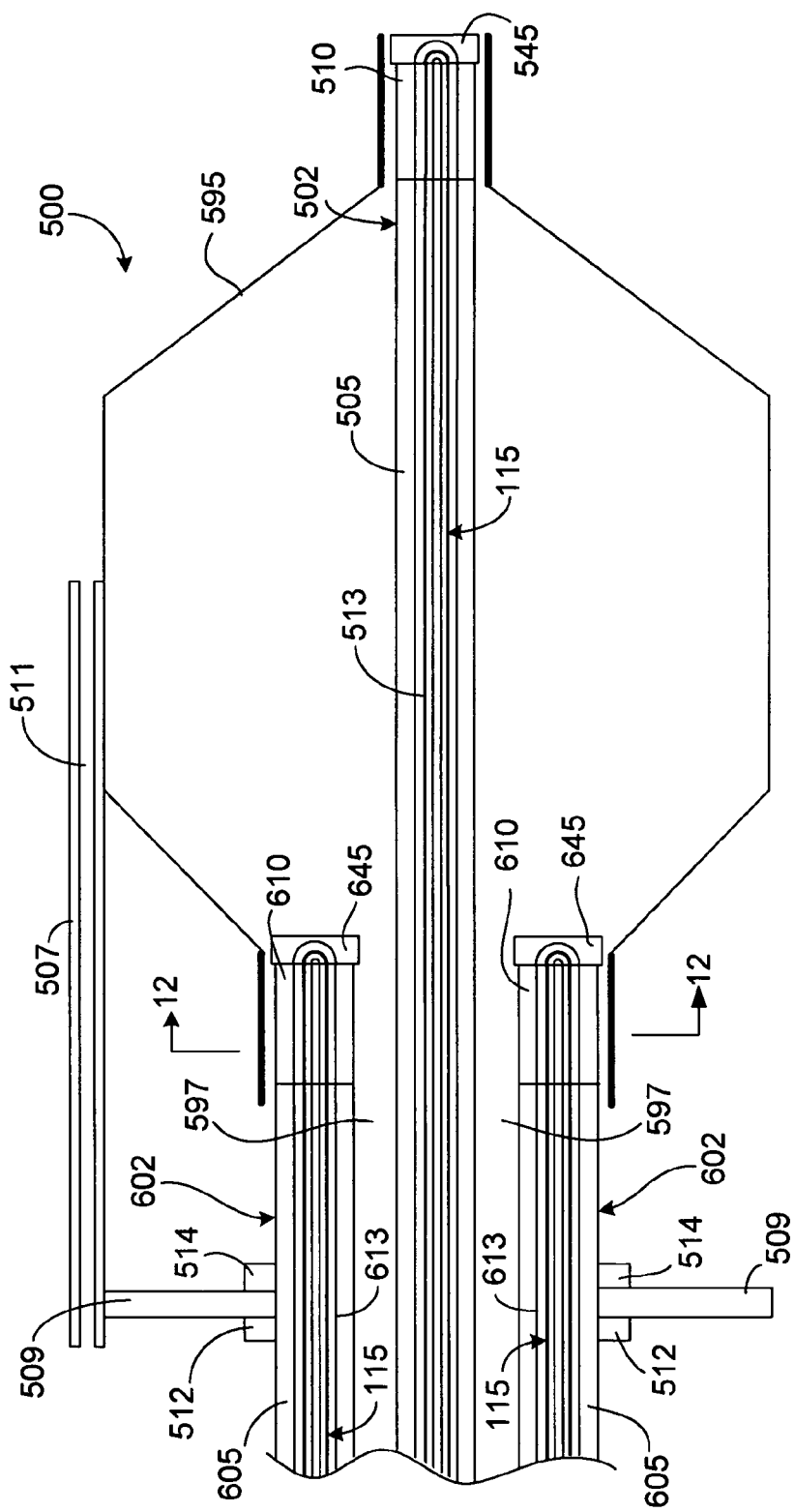
FIG. 11 is a partial cross-sectional view of an embodiment of a medical system including an inflated balloon surrounding inner and outer members including expandable regions.
Figure 12:
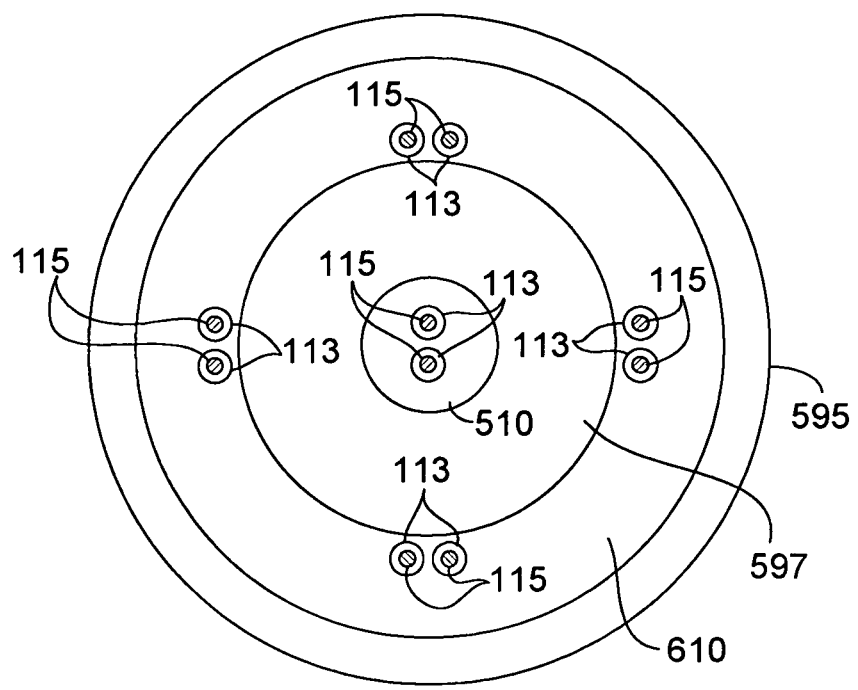
FIG. 12 is a cross-sectional view of the medical system of FIG. 11 taken along line 12-12.

While the embodiments described above relate to various types of elongate members, other types of medical devices and systems are contemplated. Referring to FIGS. 11 and 12, for example, a medical system 500 includes an inner member 502, an outer member 602, and a rotatable, expandable balloon 595 disposed around the inner and outer members. System 500 also includes a secondary guidewire housing 507 having a distal region that is attached to balloon 595, and a proximal region that is attached to a collar 509 disposed around outer member 602. Collar 509 has an inner diameter that is greater than the outer diameter of outer member 602. Therefore, collar 509 is free to rotate about outer member 602. Ring members 512 and 514 are attached, in an axially fixed arrangement, to outer member 602 on either side of collar 509. Thus, collar 509 can be prevented from being axially displaced about outer member 602.

An outer surface of inner member 502 and an inner surface of outer member 602 define a lumen 597 therebetween that can be used to inflate balloon 595. For example, an inflation fluid can be injected through lumen 597 and into an interior region of balloon 595 in order to inflate the balloon. Inner member 502 can be a substantially solid cylindrical member that defines a lumen 513 adapted to receive a wire. Inner member 502 is disposed between a distal end cap 545 and a proximal end cap (not shown). Inner member 502 includes a relatively rigid, proximal portion 505, and a relatively-compliant distal portion 510. A wire 115 extends through lumen 513 substantially along a central axis of inner member 502, and is attached to distal end cap 545 and to the proximal end cap.

Outer member 602 can be a tubular member that is disposed between a distal end cap 645 and a proximal end cap (not shown). Outer member 602, like inner member 502, includes a relatively rigid, proximal portion 605, and a relatively compliant distal portion 610. Multiple wires 115 extend through lumens 613 defined by an inner region of outer member 602 and are attached to distal end cap 645 and the proximal end cap, as shown in FIG. 12. Wires 115 are arranged substantially symmetrically about a central axis of outer member 602. System 500 further includes an energy source (not shown) that is electrically connected to wires 115.

Figure 13A:
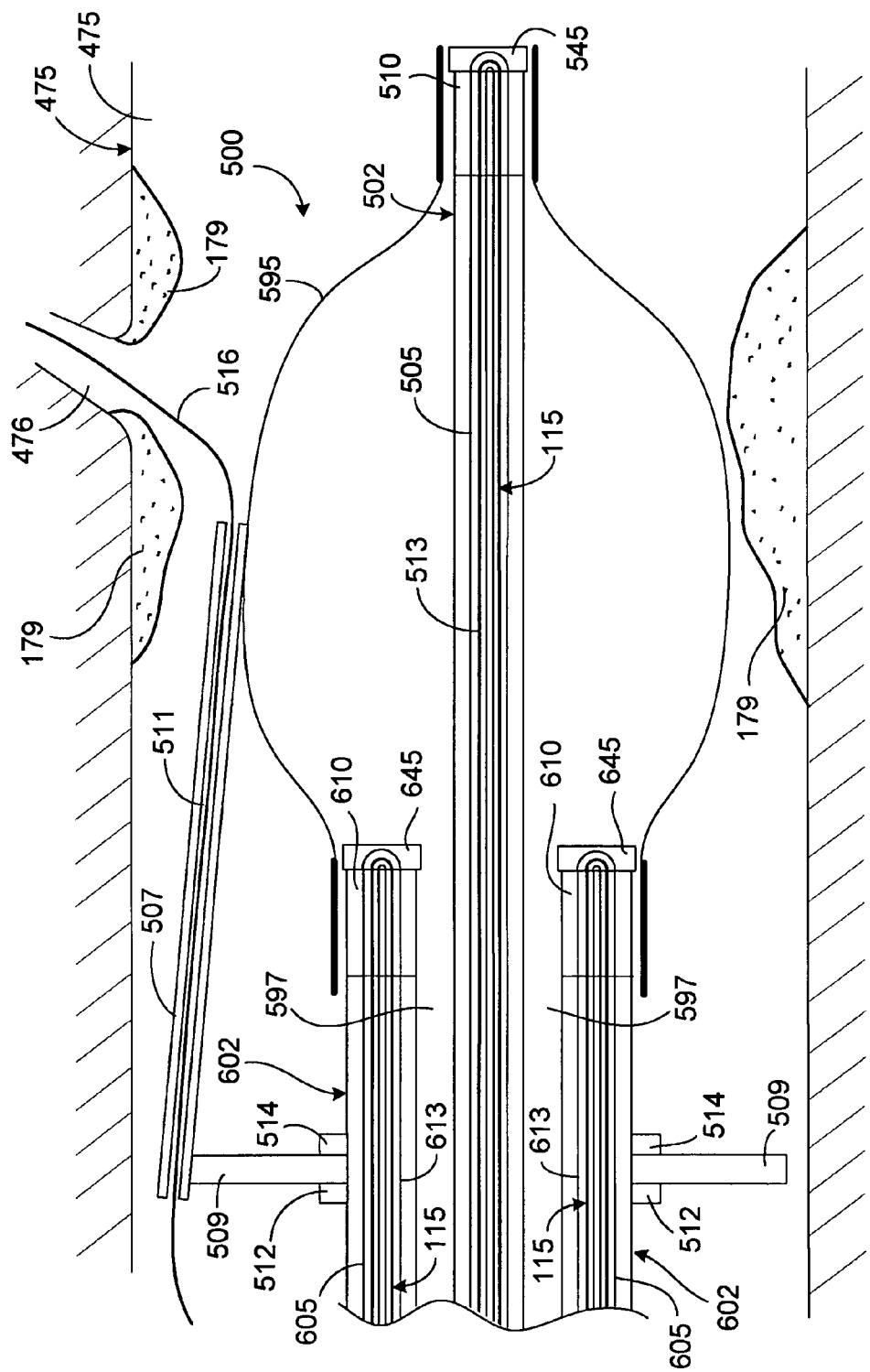
FIGS. 13A and 13B illustrate an embodiment of a method of using the medical system of FIG. 11.
Figure 13B:
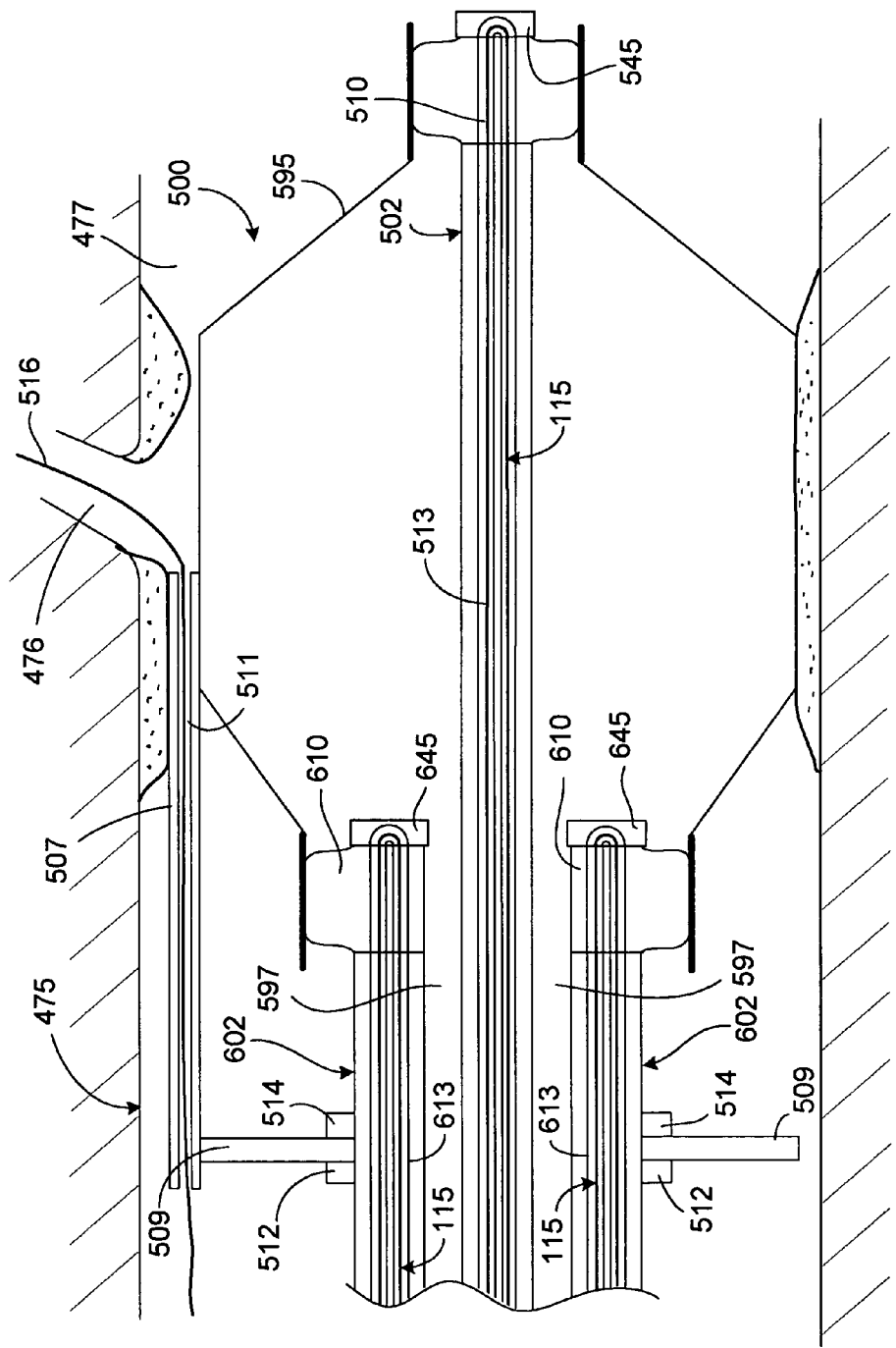

During use, as shown in FIG. 13A, a secondary guidewire 516 is positioned within branch 476 of blood vessel 475, and then a distal region of system 500 is advanced over secondary guidewire 516 until the distal region of system 500 is positioned in a desired region of blood vessel 475 (e.g., the region of blood vessel 475 from which branch 476 extends). As the system is advanced through vessel 475, balloon 595 tracks the path of secondary guidewire 516. Balloon 595 can rotate as it follows the path of secondary guidewire 516 in order to become properly aligned within vessel 475. When introduced into blood vessel 475, balloon 595 is generally in a deflated state (as shown in FIG. 13A). Subsequently, the user injects inflation fluid into an interior region of balloon 595 via lumen 597 in order to inflate the balloon, and, while inflating balloon 595 (or prior to inflating balloon 595), the user activates the energy source to energize wires 115, which causes distal portions 510 and 610 of guidewires 502 and 602, respectively, to expand. As a result, distal portions 510 and 610 create fluid-tight seals with an inner surface of balloon 595, as shown in FIG. 13B, and thus help to prevent the inflation fluid from escaping through regions between the inner surface of balloon 595 and the outer surfaces of inner and outer members 502, 602. The user subsequently removes the inflation fluid from balloon 595 via lumen 597. While removing the inflation fluid, distal portions 510 and 610 can remain in an expanded state in order to help prevent bodily fluids from entering the interior region of balloon 595.

Secondary guidewire housing 507 can be formed of any of various materials. In certain embodiments, guidewire housing 507 is formed of one or more materials having sufficient rigidity to support balloon 595 and to rotate balloon 595 without experiencing substantial deformation or damage. Guidewire housing 507 can, for example, be formed of nylon 12, PET, and/or polyimide.

In certain embodiments, as shown in FIG. 13B, distal portion 610 of outer member 602 is configured to bulge substantially outwardly when expanded. In such embodiments, lumen 597 remains substantially unobstructed when distal portion 610 is expanded. Thus, balloon 595 can be inflated and/or deflated without adding substantial difficulty. As shown in FIG. 12, to enable distal portion 610 to bulge substantially outwardly, wires 115 are arranged to extend through an inner region of distal portion 610. Alternatively or additionally, an inner region of distal portion 610 can be less rigid or stiff than an outer region of distal portion 610. For example, the inner region of distal portion 610 can be formed of a more rigid material than the outer region of distal portion 610.

In some embodiments, system 500 includes an endoprosthesis (e.g., a balloon expandable stent) positioned around balloon 595. In such embodiments, the stent can be implanted within blood vessel 475 upon expanding balloon 595. The stent, for example, can include an opening in its sidewall to help reduce obstruction of blood flow through branch 476 of blood vessel 475. The stent, in such embodiments, can be positioned around balloon 595 so that secondary guidewire 516 extends through the side opening in the stent. Alternatively or additionally, the stent can be a bifurcation stent including a branch that can be disposed within blood vessel branch 476.

While the embodiments above describe systems for rotatably disposing medical balloon 595 around inner member 502 and outer member 602, other arrangements are possible. Other examples of rotatable balloons and methods of rotatably attaching balloons can be found in U.S. patent application Ser. No. 10/785,449, filed Feb. 24, 2004, and entitled "Rotatable Catheter Assembly," and U.S. patent application Ser. No. 10/915,209, filed Aug. 10, 2004, and entitled "Rotatable Catheter Assembly," which are incorporated by reference herein.

Additionally, while the embodiments above describe an inflatable balloon, any of various other types of inflatable members can alternatively or additionally be used.

Retractable Outer Member

Figure 14:
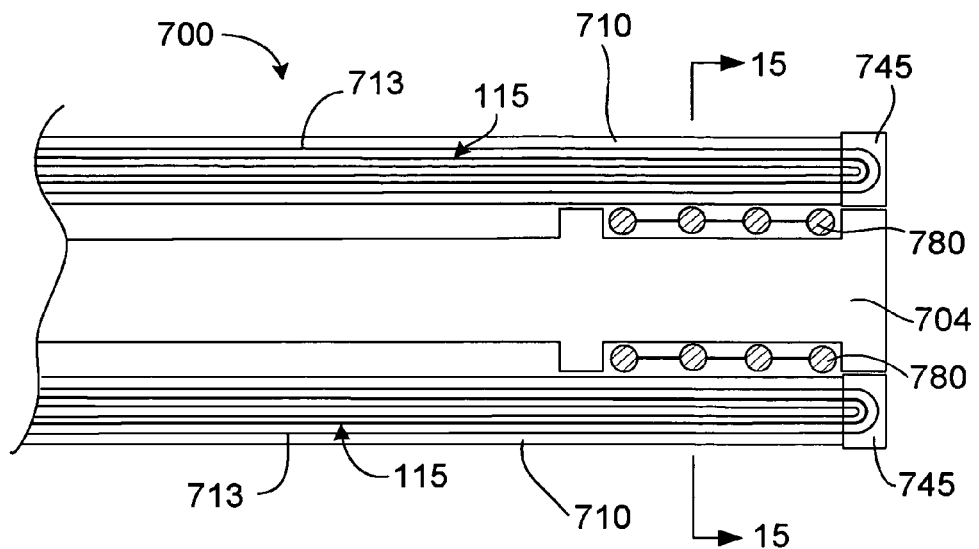
FIG. 14 is a partial cross-sectional view of an embodiment of a medical system including a retractable outer member.
Figure 15:
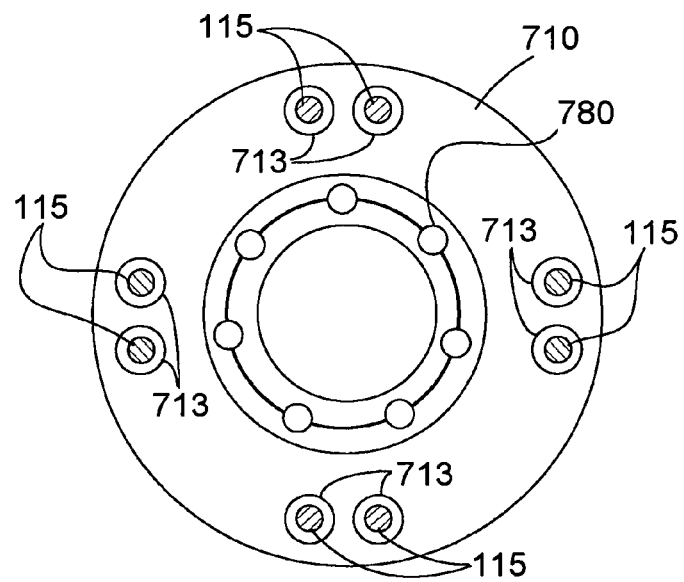
FIG. 15 is a cross-sectional view of the medical system of FIG. 14 taken along line 15-15.

Referring to FIGS. 14 and 15, a medical system 700 includes an inner member 704 on which a stent 780 (e.g., a self-expanding stent) is carried, and an outer member 710 that surrounds inner member 704 and retains stent 780 therein. Outer member 710 is attached to a distal end cap 745 and a proximal end cap (not shown). Outer member 710 is less rigid than the end caps to which it is attached on either end. Multiple wires 115 extend through lumens 713 defined by outer member 710 and are attached to distal end cap 745 and the proximal end cap. Wires 115 are arranged substantially symmetrically about a central axis of outer member 710, as shown in FIG. 15. An energy source (not shown) is electrically connected to wires 115 at a proximal end of system 700.

Figure 16A:
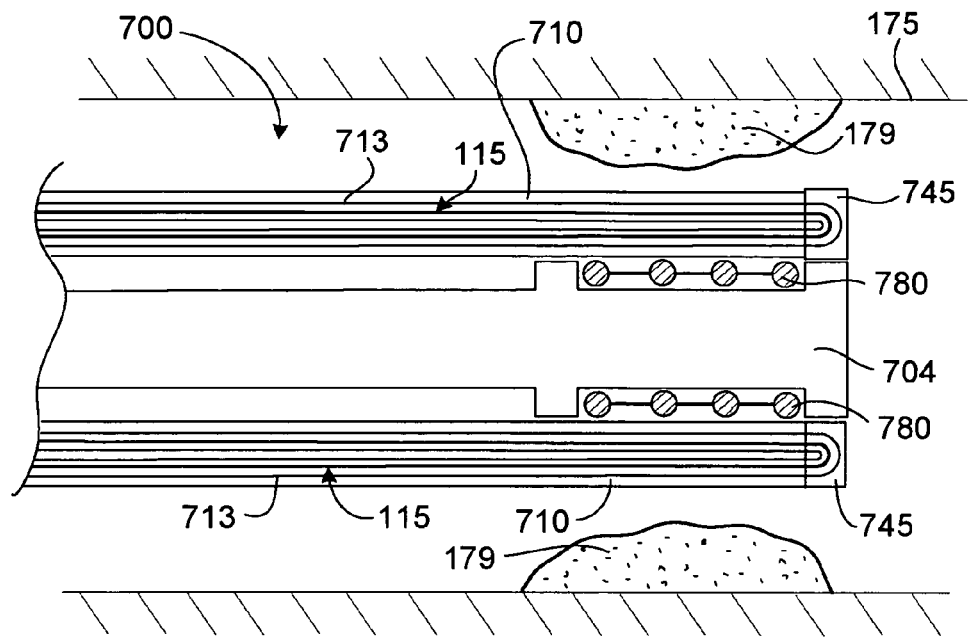
FIGS. 16A and 16B illustrate an embodiment of a method of using the medical system of FIG. 14.
Figure 16B:
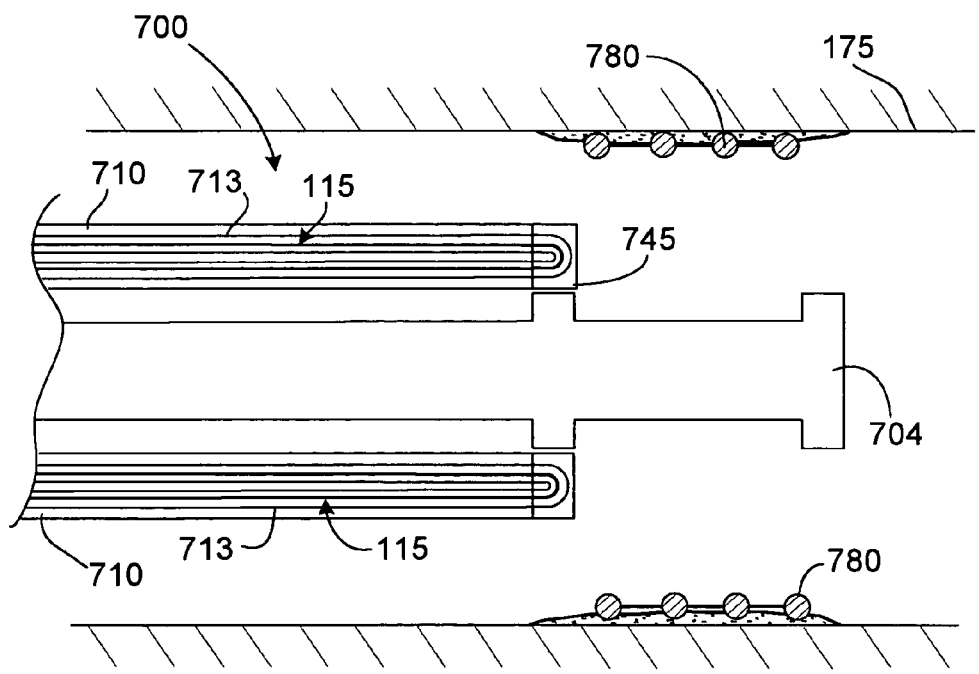

During use, as shown in FIGS. 16A and 16B, a distal region of system 700 is introduced into a blood vessel 175 of a subject, and is positioned in a desired region of blood vessel 175 (e.g., in an occluded region 179 of blood vessel 175 in which it is desired to implant stent 780). Subsequently, the user activates the energy source in order to apply a voltage across wires 115, causing distal end cap 745 to move proximally. Thus, outer member 710 is retracted from the distal portion of inner member 704 (e.g., the region of inner member 704 about which stent 780 is carried). After outer member 702 is retracted, stent 780 is released from inner member 704 and implanted within the blood vessel, as shown in FIG. 16B. Outer member 710 can then be substantially returned to its original dimensions (e.g., surrounding substantially the entire length of inner member 704), and system 700 can be withdrawn from blood vessel 175 of the subject. Alternatively, system 700 can be withdrawn from blood vessel 175 without allowing outer member 710 to return to its original dimensions.

Outer member 710 can be formed of any of the various materials discussed above with respect to distal portion 110 of system 100 shown in FIG. 1. In some embodiments, a distal portion of outer member 710 (e.g., the region of outer member 710 that surrounds stent 780) is more rigid than a proximal portion of outer member 710. In certain embodiments, for example, outer member 710 includes a relatively rigid distal tube that is attached to a relatively compliant proximal tube. The distal tube can, for example, be formed of a material that is generally more rigid that the material from which the proximal tube is formed. Alternatively or additionally, outer member 710 can be formed using any of various other techniques, such as interrupted layer co-extrusion techniques, to provide a gradual transition along the length of the outer member from a relatively flexible material to a relatively rigid material. The increased rigidity of the distal portion can help to better retain stent 780 therein. The relatively rigid, distal portion can be formed of any of the various materials discussed above with respect to proximal portion 105 of system 100 in FIG. 1.

While wires 115 have been described above as being attached to the end caps, wires 115 can alternatively or additionally be attached to one or more regions of outer member 710. For example, wires 115 can be encapsulated within the material from which outer member 710 is formed. Any of various techniques can be used to encapsulate wires 115 within outer member 710. In some embodiments, for example, wires 115 are fed through an extruder along with the material from which outer member 710 is formed.

Retractable and Expandable Outer Member

Figure 17:
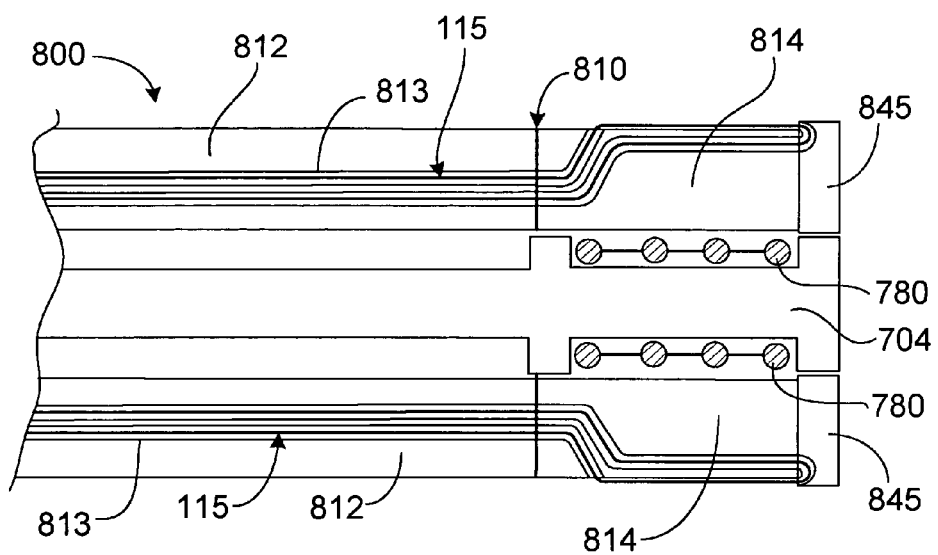
FIG. 17 is a partial cross-sectional view of an embodiment of a medical system including an expandable outer member.

In some embodiments, an outer member (e.g., a sheath) is configured to expand radially in addition to or as an alternative to contracting axially. Referring to FIG. 17, for example, a medical system 800 includes inner member 704 on which stent 780 is carried, and an outer member 810 that surrounds inner member 704 and retains stent 780 therein. Outer member 810 is positioned between and attached to a distal end cap 845 and a proximal end cap (not shown). Outer member 810 includes a relatively rigid, proximal portion 812 and a relatively compliant, distal portion 814. Multiple wires 115 extend about the length of outer member 810 and are attached to an outer region (e.g., an outer surface) of distal end cap 845 and to the proximal end cap. Wires 115 are disposed within a wall of proximal portion 812 and extend along an outer surface of distal portion 814. System 800 also includes an energy source (not shown) that is electrically connected to wires 115 at a proximal end of system 800.

Figure 18A:
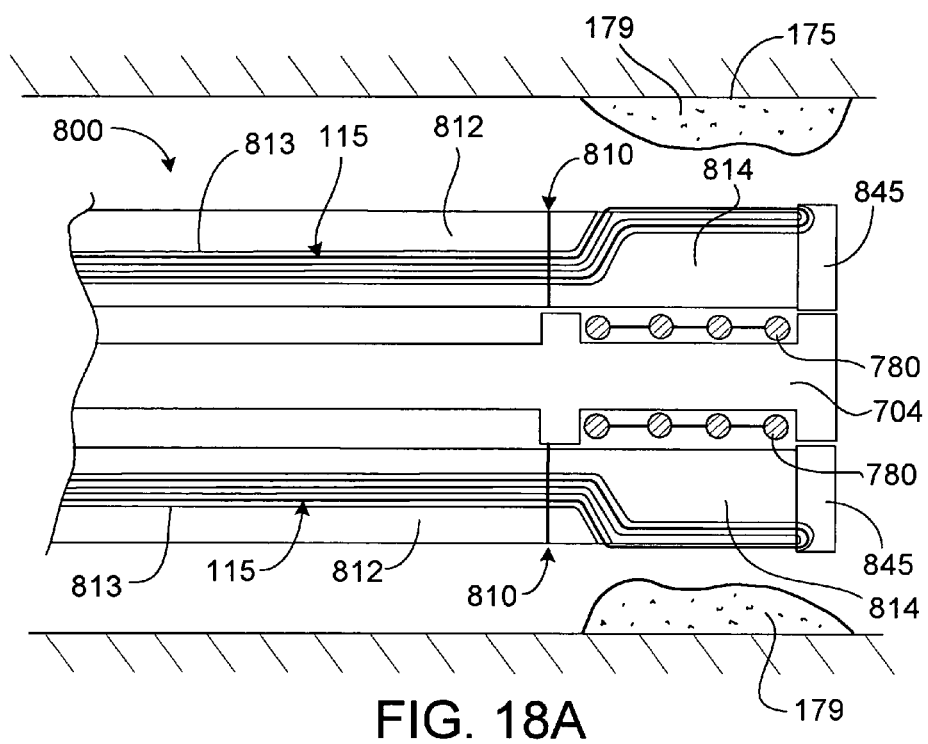
FIGS. 18A and 18B illustrate an embodiment of a method of using the medical system of FIG. 17.
Figure 18B:
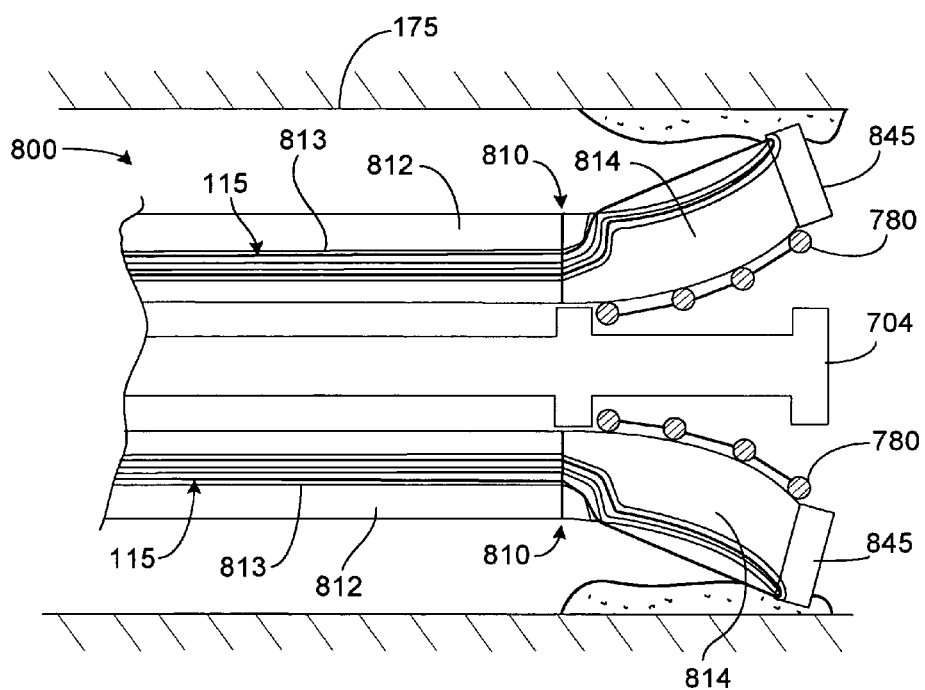

System 800 can be used in a similar manner to system 700 described above. Referring to FIGS. 18A and 18B, for example, a distal region of system 800 is positioned within a desired region of blood vessel 175 (e.g., within occluded region 179 of blood vessel 175). Subsequently, the user activates the energy source to apply a voltage across wires 115, causing wires 115 to heat and contract. As wires 115 contract, distal portion 814 of outer member 810 expands radially and contracts axially, as shown in FIG. 18B. For example, wires 115 can pull the outer region of distal end cap 845 proximally. This action causes distal portion 814 of outer member 810 to fan out radially. As distal portion 814 is radially expanded and axially retracted, stent 780 is released from inner member 704 in a controlled manner. For example, stent 780 can gradually expand from its distal end to its proximal end. This can reduce the likelihood of stent 780 "jumping" from inner member 704. As a result, stent 780 can be more accurately and/or precisely positioned within blood vessel 175 of the subject. Once stent 780 has been implanted within blood vessel 175, the user deactivates the energy source thereby allowing wires 115 to cool and allowing outer member 810 to approximately return to its original dimensions (e.g., surrounding substantially the entire length of inner member 704), and system 800 is withdrawn from blood vessel 175.

Proximal portion 812 of outer member 810 can be formed of any of the various relatively rigid materials discussed above with respect to proximal portion 105 of system 100 in FIG. 1. Distal portion 814 can be formed of any of the various relatively compliant materials discussed above with respect to distal portion 110 of system 100 in FIG. 1.

In some embodiments, distal portion 814 of includes axial slits along its inner surface. The slits can facilitate the radial expansion of distal portion 814. For example, the axial slits can increase in width as distal portion 814 expands, and can, therefore, reduce the resistance that distal portion 814 encounters as it expands.

While wires 115 are described above as extending along an outer surface of distal portion 814, wires 115 can alternatively or additionally be disposed within a wall of distal portion 814. For example, wire 115 can be disposed within an outer region of the wall. As a result, the contraction of wires 115 can cause distal portion 814 of outer member 810 to fan out radially, in a manner similar to that described above.

While certain embodiments have been described above, other embodiments are possible.

As an example, while the wires of the embodiments above are shown as having a substantially circular cross-section, the wires can alternatively or additionally have any of various other cross-sectional shapes, such as rectangular, square, triangular, oval, tubular, and semi-circular.

As another example, while wires have been shown as being of a substantially unitary construction, other arrangements are possible. In some embodiments, for example, wires include a conductive portion and a ground portion. The conductive portion can be formed of any of various materials that contract when exposed to electrical energy, such as a nickel-titanium alloy. The ground portion can be formed of any of various materials that are capable of conducting electricity and/or heat, and that dissipate less heat when electrically or thermally charged than the material from which the conductive portion is formed. Examples of such materials include gold, and platinum. The conductive portion is electrically connected to the ground portion. By forming the ground portion of one or more materials that dissipate less heat than the material from which the conductive portion is formed, the overall dissipation of heat within the medical device can be reduced. This can be beneficial because limiting heat dissipation within the medical device can lead to improved results of some of the medical treatments described herein.

As an additional example, in some embodiments, the conductive portion of the wire comprises about 50 percent or more (e.g., about 75 percent or more, about 100 percent) of the length of the wire. In certain embodiments, the conductive portion comprises about 50 percent or less (e.g., about 25% or less, about ten percent or less) of the length of the wire. The intensity and/or amount of contraction of the wire can be a function of the length of the conductive portion. Therefore, contraction can be controlled by varying the length of the conductive portion.

Figure 19:
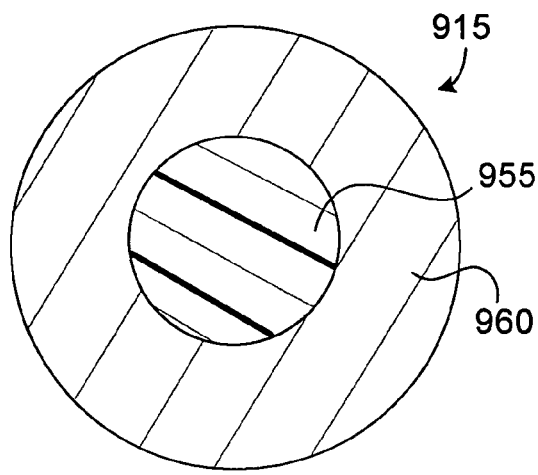
FIG. 19 is a cross-sectional view of an embodiment of a wire of a medical system.

As a further example, in certain embodiments, the conductive portion of the wire and the ground portion of the wire are concentrically arranged about one another. As shown in FIG. 19, for example, a wire 915 includes a ground portion 960 that is arranged along an outer surface of a conductive portion 955. In certain embodiments, an insulative layer (not shown) is positioned between conductive portion 955 and ground portion 960. This arrangement can help to reduce the overall volume occupied by the wire within the medical devices described herein. Consequently, this arrangement can contribute to a reduction in the overall profile of the medical devices. Furthermore, because ground portion 960, which dissipates less heat than conductive portion 955, is arranged around an outer perimeter of conductive portion 955, ground portion 960 can help to prevent dissipation of heat from conductive portion 955 into a bodily vessel (e.g., a blood vessel) of a subject during use. Any of various methods can be used to form wire 915. As an example, a ground material (e.g., gold) can be sputtered onto the outer surface of a conductive element (e.g., a nickel-titanium alloy wire). In certain embodiments, the conductive portion can be arranged to surround the ground portion.

As another example, while the embodiments above describe a wire extending substantially the full length of a medical device (e.g., from a proximal end cap to a distal end cap), other arrangements are possible. In some embodiments, for example, the wire can be positioned to extend only part way through or about a relatively compliant, distal portion of the medical device. In certain embodiments, multiple wires terminate at staggered positions about the length of the medical device. For example, the multiple wires can be staggered within or about the compliant distal portion. Consequently, those regions of the distal portion in which the wires extend to more distal points contract more than those regions in which the wires extend to more proximal points. This arrangement can be used, for example, to change the shape of the distal portion (e.g., to create curvature within the distal portion). In embodiments in which the wire(s) extends less than the full length of the elongate member, a conductive element (e.g., a copper element) can be attached to both the wire(s) and the energy source. Consequently, energy can be applied to the wire(s) without directly connecting the wire(s) to the energy source located at the proximal end of the elongate member.

As an additional example, in some embodiments, rather than extending loosely through channels or lumens defined by the medical device, the wire can be encapsulated within the medical device. In such embodiments, a compliant portion of the medical device in which the wire is encapsulated can expand and contract along with the wire. In certain embodiments, the wire is encapsulated along only a portion of its length, such that the remaining portion of its length is free to move within a channel defined by the medical device.

As a further example, while the embodiments discussed above involve applying electrical energy to the wire, other forms of energy can be used. Other examples of energy include thermal energy (e.g., hot fluid), magnetically induced currents (e.g., RF fields), microwave energy, laser energy, and ultrasound energy.

As another example, in certain embodiments, as an alternative to or in addition to applying one or more of the above-noted types of energy to the wire, a mechanical force can be applied to the wire. For example, the wire can be attached to a mechanical device at a proximal end region of the medical system, and the mechanical device can be configured to pull proximally on the wire. Any of various mechanical devices capable of applying a force (e.g., a pulling force) to the wire can be used. Examples of such mechanical devices include lever handles and screws. In embodiments that utilize mechanical force, rather than other forms of energy (e.g., electrical and/or thermal), the wire can be formed of a wide range of materials in addition to those described above. Examples of such materials include metallic alloys (e.g., stainless steel), polymer fibers (e.g., dracon, HDPE, nylon), and ceramic fibers.

As an additional example, in certain embodiments, rather than contracting in response to being exposed to certain forms of energy, the wire can be configured to expand in response to being exposed to energy. For example, the wire can be formed of a material that expands in response to the application of electrical and/or thermal energy. In such embodiments, a distal portion of the medical device, for example, can be arranged to expand in response to the expansion of the wire. For example, the wire can be attached to a proximal portion of the medical device, and, upon applying energy to the wire, the proximal portion of the medical device can cooperate with a distal end cap, which is more rigid than the distal portion, to compress the distal portion therebetween. Consequently, the distal portion can be expanded.

As a further example, in some embodiments, the medical device (e.g., the elongate member, the balloon sealing member, and/or the outer member) includes a fluid-cooled channel (e.g., a water-cooled channel) to increase the rate at which the wire cools after being exposed to energy (e.g., electrical and/or thermal energy). The fluid-cooled channel, for example, can extend adjacent the wire within the proximal portion and/or the distal portion of the medical device. In some embodiments, fluid is continuously circulated through the channel. Thus, heat dissipated by the wire can be absorbed by the fluid within the channel. Consequently, the likelihood of heat dissipating from wire into the surrounding area of a blood vessel during use can be reduced.

As another example, while the embodiments above show the power source as being electrically connected to the wire at end regions of the wire, the power source can be electrically connected to the wire at any point along the length of the wire.

As an additional example, while the embodiments above describe the wire as extending through a medical device, the wire can alternatively or additionally extend about an outer or inner surface of the medical device.

As a further example, while many of the embodiments described herein include a distal portion of a medical device that is relatively compliant and a proximal portion that is relatively rigid, in some embodiments, the distal portion can be relatively rigid and the proximal portion can be relatively compliant.

As another example, while in some of the embodiments described above, the medical devices have been described as substantially solid, cylindrical members, the medical devices can alternatively or additionally be any of various other shapes, such as tubular, rectangular, semi-circular, and/or triangular.

As an additional example, while the embodiments above show the medical systems being used in a blood vessel of a subject, the systems can alternatively or additionally be used within any of various other bodily vessels or cavities of a subject. For example, the systems can be used within pulmonary vessels, gastrointestinal vessels, urinary vessels, reproductive vessels, biliary vessels, lymphatic vessels, the thoracic cavity (e.g., the heart, the lungs, the trachea, the esophagus, large blood vessels), the abdominal cavity (e.g., the gastrointestinal tract, the kidneys), the pelvic cavity (e.g., the urogenital system, the rectum), and the cranial cavity (e.g., the brain, vertebral canal).

As a further example, while embodiments have been described in which the therapeutic agent is paclitaxel, one or more other therapeutic agents can alternatively or additionally be used. Therapeutic agents include agents that are negatively charged, positively charged, amphoteric, or neutral. Therapeutic agents include genetic therapeutic agents, non-genetic therapeutic agents, and cells, and can be negatively charged, positively charged, amphoteric, or neutral. Therapeutic agents can be, for example, materials that are biologically active to treat physiological or pathological conditions;

pharmaceutically active compounds; gene therapies; nucleic acids with and without carrier vectors; oligonucleotides; gene/vector systems; DNA chimeras; compacting agents (e.g., DNA compacting agents); viruses; polymers; hyaluronic acid; proteins (e.g., enzymes such as ribozymes); immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation); calcium entry blockers; and survival genes which protect against cell death. In certain embodiments, the therapeutic agent is an immunosuppressant, such as sirolimus. Additional examples of therapeutic agents can be found in U.S. patent application Ser. No. 11/111,511, filed Apr. 21, 2005, and entitled "Particles," which is incorporated by reference herein.

While various dimensions of medical systems and medical system components are described herein, any of various other dimensions are possible.

The following example illustrates methods of making and using an embodiment of a medical system.

EXAMPLE 1

A first stock tube is extruded from high-durometer Tecothane® 75D polyurethane. The Tecothane® 75D polyurethane is extruded using a 12.7 millimeter (0.5 inch) Brabender extruder with a temperature of 199 degrees Celsius in the feeding zone, 216 degrees Celsius in zone 2, and 227 degrees Celsius in zones 3 and 4. The first stock tube is made with an inner diameter of 0.48 millimeter and an outer diameter of one millimeter. A second stock tube is extruded from low-durometer Tecothane® 74A polyurethane to have the same dimensions as the first tube. The extrusion of the second stock tube is carried out using the same process described above. However, the temperature in the feeding zone is 199 degrees Celsius and the temperature in zones 2, 3, and 4 is 216 degrees Celsius.

After forming the first and second stock tubes, a 100 cm section, a 130 millimeter section, and a 20 millimeter section are cut from the first stock tube. A 10 millimeter section is cut from the second stock tube. As described below, the 100 centimeter section and the 130 millimeter section are attached to one another to form a relatively rigid, proximal tube of a medical system. The 10 millimeter section of the second stock tube is attached to the distal region of the proximal tube to form an expandable member of the medical system, and the 20 millimeter section of the first stock tube is attached to the distal end of the expandable member. The 20 millimeter section is later reduced in length, as described below, to form an end cap of the medical system. Cutting of the tubes is performed using a device called a razor blade guillotine, whereby the tube is held in a V-shaped groove annex ruler and a razor blade is slid vertically in a holder through a slit in the V-shaped groove.

After forming the discrete tubular sections, the 130 millimeter section, the 10 millimeter section, and the 20 millimeter section are positioned over a 0.48 millimeter stainless steel mandrel such that the distal end of the 130 millimeter section abuts the proximal end of the 10 millimeter section, and the distal end of the 10 millimeter section abuts the proximal end of the 20 millimeter section. A heat shrink sleeve is then mounted over the abutted ends, and the tubular structure is heated to a temperature of about 210 degrees Celsius using a $CO_2$ laser. The heat shrink sleeve functions to hold the tubular sections together while the abutted ends become welded together from the heat. The mandrel and heat shrink tube are then removed, and the 20 millimeter section is cut to a length of two millimeters using the cutting process described above to form the end cap of the medical system.

A first polyester-coated copper transformer wire (available from Comax of West Yorkshire, England) having a length of two meters and a diameter of 0.10 millimeter is positioned in a parallel configuration to a Flexinol® nickel-titanium alloy wire that has a diameter of 0.25 millimeter and a length of 140 millimeters. The polyester coating of the copper wire can sustain a temperature of up to about 200 degrees Celsius. A few millimeters of the polyester sleeve at one end of the copper wire is then removed. This stripped end of the copper wire is then bent into a U-shaped configuration and positioned against the distal end of the Flexinol® nickel-titanium alloy wire. It is then soldered to the distal end of the Flexinol® nickel-titanium alloy wire. The distally attached copper wire is then wound ten times tightly around the Flexinol® nickel-titanium alloy wire such that it is equally distributed over the 130 mm section, which allows it to expand outwardly as the 10 mm section is reduced in length, as discussed below. The remaining length of the first copper wire extends proximally beyond the proximal end of the Flexinol® nickel-titanium alloy wire. A stripped end of a second copper wire having the same dimensions as the first copper wire is then soldered to the proximal end of the Flexinol® nickel-titanium alloy wire. The first copper wire and the Flexinol® nickel-titanium alloy wire are inserted through the lumen defined by the tubular sections, beginning with the 130 mm section. The Flexinol® nickel-titanium alloy wire and the copper wire are positioned within the lumen such that the Flexinol® nickel-titanium alloy wire and the bent region of the copper wire are flush with the distal end of the end cap. The ends of the Flexinol® nickel-titanium alloy wire are then secured within the lumen using cyano acrylate glue. In particular, the distal end region of the Flexinol® nickel-titanium alloy wire is glued to the end cap, and the proximal end region of the Flexinol® nickel-titanium alloy wire is glued to the proximal end of the 130 millimeter section of the proximal tube.

After attaching the end regions of the Flexinol® nickel-titanium alloy wire to the end cap and the 130 millimeter section of the proximal tube, the free ends of the two copper wires are fed through the lumen of the 100 centimeter proximal tube portion, and the distal end of the 100 centimeter tube section is butt welded to the proximal end of the 130 millimeter tube section to form the relatively rigid, proximal tube of the medical system. Due to the length of the copper wires, the ends of the copper wires extend from a proximal opening of the lumen. The ends of the copper wires are connected to a 1.5 volt AAA battery.

To operate the medical system, 1.5 volts is applied across the copper wires by the battery, sending a current of about 0.085 Amps through the Flexinol® nickel-titanium alloy and copper wires. The voltage is applied across the wires for about one second, causing the temperature of the Flexinol® nickel-titanium alloy wire to increase from about 37 degrees Celsius to about 114 degrees Celsius. As a result of the temperature increase, the Flexinol® nickel-titanium alloy wire contracts by about four percent of its length (i.e., by about 5.2 millimeters). The expandable member contracts to a length of about 5.0 millimeters (50% of its original length), causing it to expand radially to a diameter of about 1.4 millimeter.

Other embodiments are within the scope of the following claims.

What is claimed is:

1. A medical system comprising:
an electrical energy source;
an elongate shaft having a lumen defined therein;
wherein the lumen extends continuously from a proximal end of the elongate shaft to a distal end region of the elongate shaft and through a turn as the lumen loops back to the proximal end of the elongate shaft, wherein the lumen has walls extending uninterrupted from the proximal end of the elongate shaft to the distal end region of the elongate shaft, through the turn and back to the proximal end;
an expandable member disposed at a distal portion of the shaft; and
a wire associated with the expandable member, the wire extending from the electrical energy source, through the lumen from the proximal end of the elongate shaft to the distal end region of the elongate shaft, through the expandable member, and loops back through the lumen to the proximal end of the elongate shaft, the wire having a first state in which the expandable member is unexpanded, and the wire having a second state in which the expandable member is expanded;
wherein the wire contracts in length from the first state to the second state as a result of heating the wire by applying an electrical current through the wire with the electrical energy source.

2. The medical system of claim 1, wherein the expandable member comprises a tubular member.

3. The medical system of claim 1, wherein the wire is attached to the expandable member.

4. The medical system of claim 1, wherein the wire comprises a shape-memory alloy.

5. The medical system of claim 1, further comprising a first member adjacent the expandable member, the expandable member being less rigid than the first member.

6. The medical system of claim 5, wherein the first member is positioned adjacent a distal end of the expandable member.

7. The medical system of claim 5, wherein the wire is attached to the first member.

8. The medical system of claim 5, further comprising a second member, the expandable member extending between the first and second members.

9. The medical system of claim 8, wherein the expandable member is less rigid than the second member.

10. The medical system of claim 8, wherein the second member is positioned adjacent a proximal end of the expandable member.

11. The medical system of claim 8, wherein the wire is attached to the second member.

12. The medical system of claim 5, wherein the first member has a flexural modulus that is at least about ten times greater than a flexural modulus of the expandable member.

13. The medical system of claim 5, wherein the first member comprises at least one material selected from the group consisting of polytetrafluoroethylene, polyether-block co-polyamide polymers, copolyester elastomers, thermoplastic polyester elastomers, thermoplastic polyurethane elastomers, polyeolefins, high-density polyethylene, low-density polyethylene, and polyamides.

14. The medical system of claim 1, wherein the expandable member comprises at least one material selected from the group consisting of silicone, polyether-block co-polyamide polymers, polyesters, polysulfones, polytetramethylene glycol, and polyurethane.

15. The medical system of claim 1, wherein the expandable member is formed of a porous material.

16. The medical system of claim 15, wherein pores of the expandable member contain a therapeutic agent.

17. The medical system of claim 1, wherein the expandable member defines at least one aperture and a slit extending from an outer surface of the expandable member to the aperture.

18. The medical system of claim 17, further comprising a therapeutic agent disposed within the at least one aperture.

19. The medical system of claim 1, wherein the lumen is a single continuous lumen.

20. The medical system of claim 1, wherein the lumen has a first opening at the proximal end of the shaft and a second opening at the proximal end of the shaft and positioned adjacent to the first opening.

* * * * *